United States Patent
Muise et al.

(10) Patent No.: US 11,110,227 B2
(45) Date of Patent: Sep. 7, 2021

(54) METHOD AND APPARATUS FOR INJECTING FLUIDS

(71) Applicants: Cheryl Muise, London (CA); David Snaith, Toronto (CA); Steve A. Copeland, Barrie (CA); Mitchell Thompson, Barrie (CA)

(72) Inventors: Cheryl Muise, London (CA); David Snaith, Toronto (CA); Steve A. Copeland, Barrie (CA); Mitchell Thompson, Barrie (CA)

(73) Assignees: Cheryl Muise; Steve A. Copeland

( * ) Notice: Subject to any disclaimer, the term of this patent is extended or adjusted under 35 U.S.C. 154(b) by 250 days.

(21) Appl. No.: 16/386,830

(22) Filed: Apr. 17, 2019

(65) Prior Publication Data
US 2020/0147316 A1 May 14, 2020

Related U.S. Application Data

(60) Provisional application No. 62/758,149, filed on Nov. 9, 2018.

(51) Int. Cl.
*A61M 5/315* (2006.01)

(52) U.S. Cl.
CPC .... *A61M 5/31553* (2013.01); *A61M 5/31528* (2013.01); *A61M 5/31536* (2013.01); *A61M 5/31586* (2013.01)

(58) Field of Classification Search
CPC .......... A61M 5/31528; A61M 5/31536; A61M 5/31553; A61M 5/31555; A61M 5/31586; A61M 5/3155
See application file for complete search history.

(56) References Cited

U.S. PATENT DOCUMENTS

| | | | |
|---|---|---|---|
| 8,133,208 B2 | 3/2012 | Hetherington | |
| D690,417 S | 9/2013 | Solomon | |
| 8,672,898 B2 * | 3/2014 | Enggaard | A61M 5/20 604/211 |
| 8,808,244 B2 | 8/2014 | Adlon et al. | |
| 8,851,336 B2 | 10/2014 | Weill | |
| 9,381,307 B2 * | 7/2016 | Eaton | A61M 5/20 |
| 9,566,387 B2 | 2/2017 | Verhoeven et al. | |

(Continued)

FOREIGN PATENT DOCUMENTS

CA 2908822 9/2014

*Primary Examiner* — Quynh-Nhu H. Vu
(74) *Attorney, Agent, or Firm* — Sand, Sebolt & Wernow Co., LPA

(57) ABSTRACT

An injecting device includes a housing having a longitudinal axis extending. A dose setting member is rotatable in the housing in a first or second direction about the longitudinal axis. A plunger extends through a bore of the dose setting member and into a bore of a barrel engaged with the housing. Pushing on an arm extending through a slot in the housing rotates the dose setting member in the first direction. As it rotates, indicia on the dose setting member are progressively displayed through an aperture in the housing. An actuator is engaged to release the dose setting member to rotate in the second direction and this rotation causes the plunger to move axially within the barrel's bore and push the pre-set dose of fluid therefrom. The dose setting member remains in a constant axial position within the housing during rotation in each of the first and second directions.

19 Claims, 19 Drawing Sheets

(56) References Cited

U.S. PATENT DOCUMENTS

| | | | |
|---|---|---|---|
| 9,687,611 B2 | 6/2017 | Moeller et al. | |
| 9,821,122 B2 | 11/2017 | Sutkin et al. | |
| 10,441,724 B2 * | 10/2019 | Oakley | A61M 5/3146 |
| 2004/0033224 A1 | 2/2004 | Kirchhofer et al. | |
| 2006/0153693 A1 * | 7/2006 | Fiechter | A61M 5/3204 |
| | | | 417/63 |
| 2008/0071226 A1 | 3/2008 | Moser et al. | |
| 2008/0119796 A1 | 5/2008 | Graf et al. | |
| 2009/0221973 A1 | 9/2009 | Hommann | |
| 2012/0259289 A1 | 10/2012 | Byrnes et al. | |
| 2014/0039405 A1 | 2/2014 | Konandreas et al. | |
| 2015/0025502 A1 | 1/2015 | Spenser et al. | |
| 2015/0094667 A1 | 4/2015 | Verhoeven et al. | |
| 2016/0038687 A1 | 2/2016 | Sutkin et al. | |
| 2016/0199586 A1 * | 7/2016 | Bilton | A61M 5/31528 |
| | | | 604/189 |
| 2016/0206827 A1 * | 7/2016 | Bilton | A61M 5/31548 |
| 2016/0235924 A1 | 8/2016 | Soerensen et al. | |
| 2017/0119973 A1 * | 5/2017 | Roervig | A61M 5/31583 |
| 2017/0136188 A1 * | 5/2017 | Marsh | A61M 5/20 |
| 2017/0259005 A1 | 9/2017 | Moeller et al. | |

\* cited by examiner

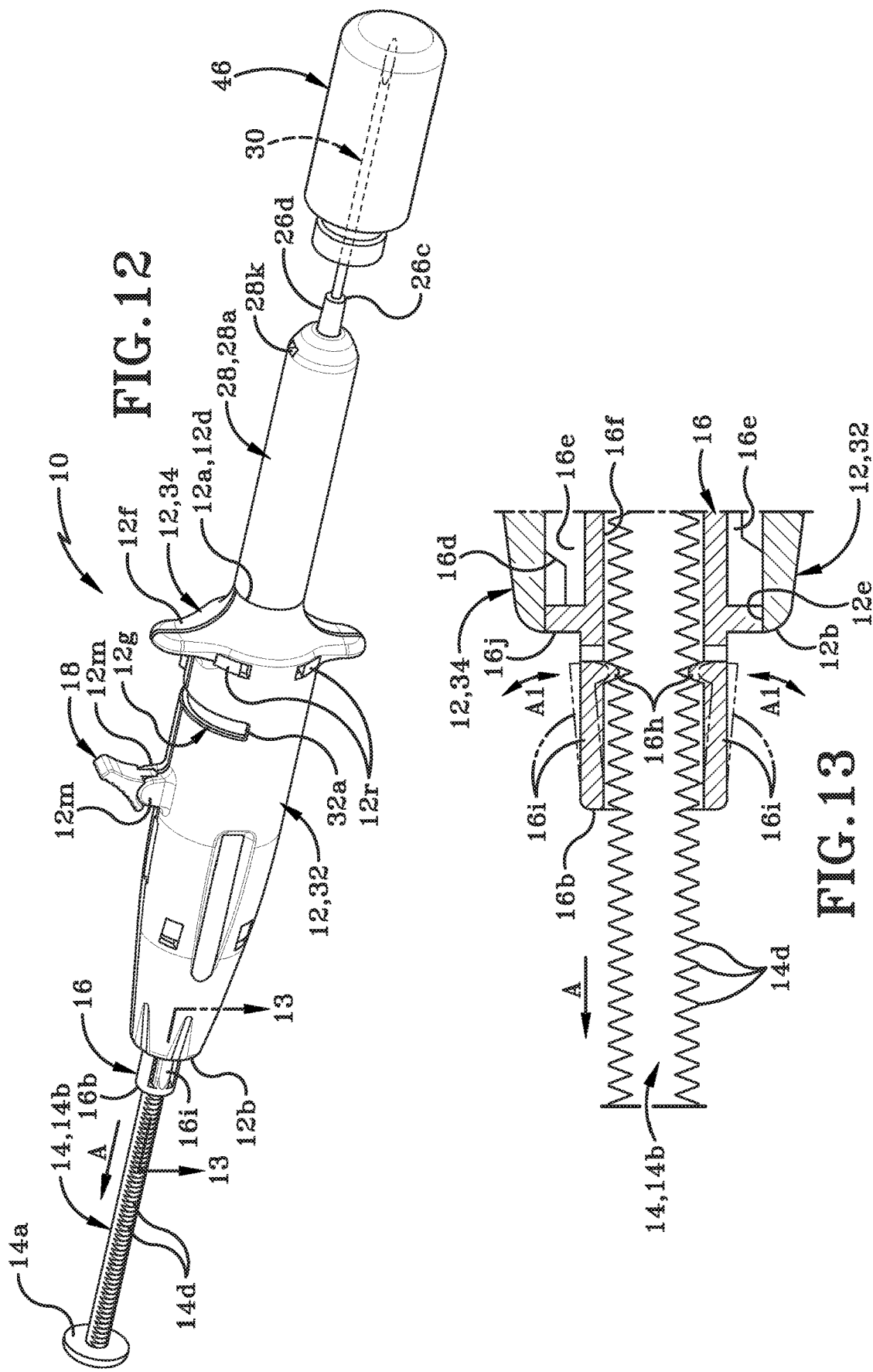

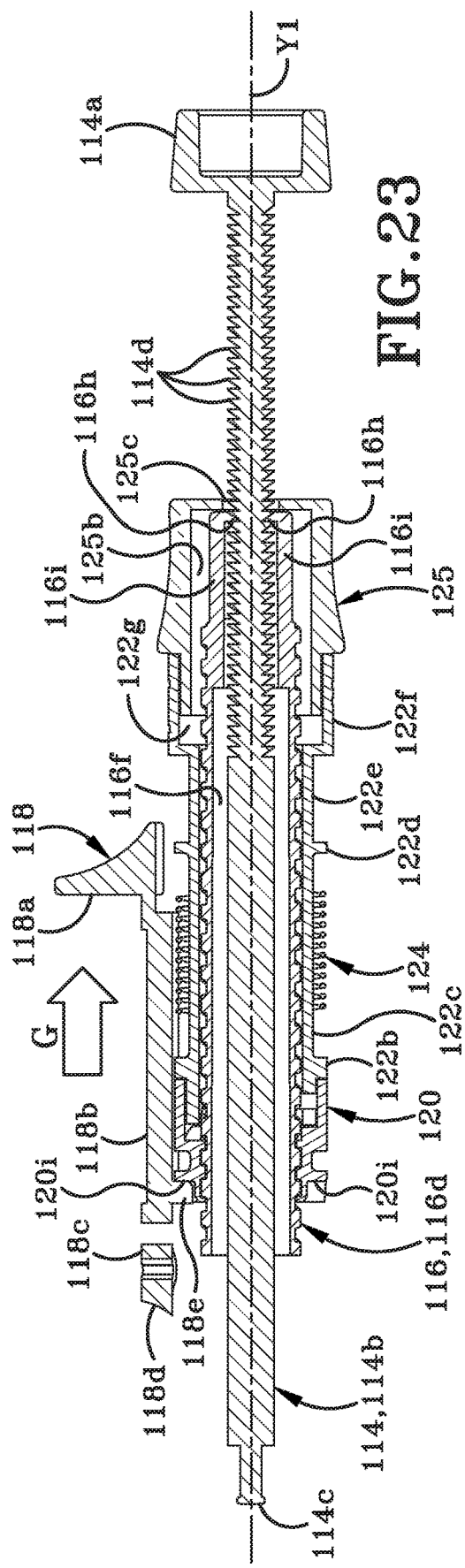
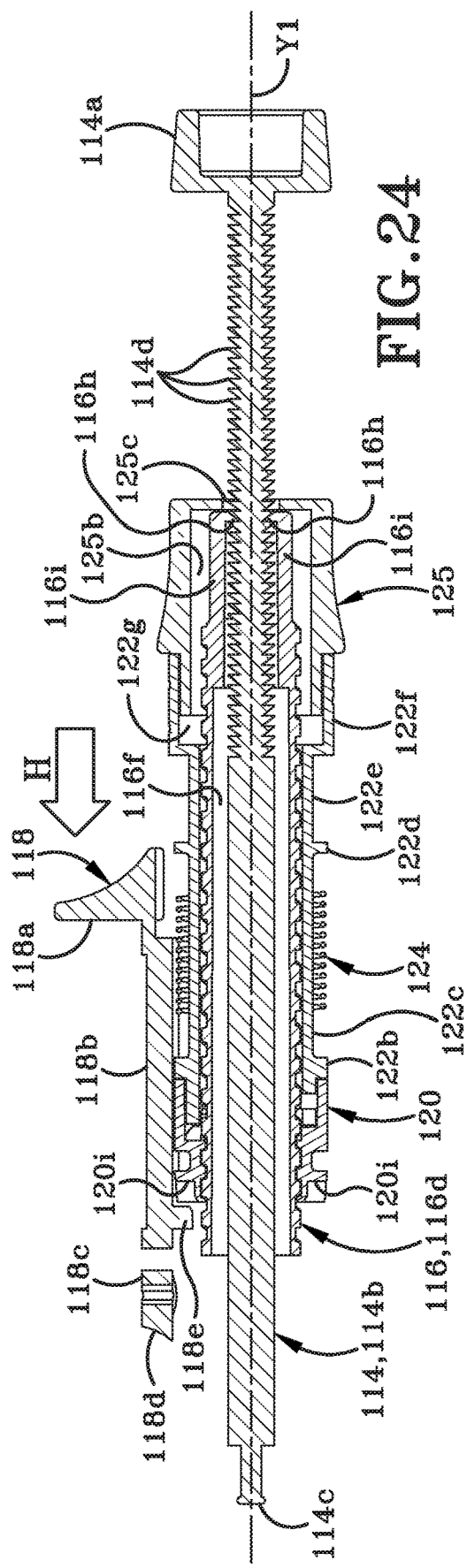

METHOD AND APPARATUS FOR INJECTING FLUIDS

CROSS-REFERENCE TO RELATED APPLICATIONS

This application claims the benefit of U.S. Provisional Patent Application Ser. No. 62/758,149, filed Nov. 9, 2018, the entire disclosure of which is incorporated herein by reference.

TECHNICAL FIELD

This disclosure is directed generally to medical equipment. More particular, this disclosure is directed to an injecting device for injecting fluids such as drugs or medication that are in liquid form. Specifically, the disclosure is directed to an injecting device that permits the loading of a full dose of liquid medication into the device and that then permits the full dose of medication to be delivered to a patient in smaller doses that are of a preselected consistent volume.

BACKGROUND

Background Information

In some methods of medical and cosmetic surgery it may be desirable to inject small quantities of a total volume of liquid medication or treatment fluid at several different locations on a person's body instead of injecting the full dose of medication at one location. BOTOX® for example has been found to be most effective when administered in this manner. (BOTOX is a registered trademark of Allergan, Inc. of Irvine Calif., USA).

One of the issues when administering small amounts of a total volume of treatment fluid is that the person performing the injections has to consistently try to deliver the same small volume of treatment fluid to each of the several locations on the person's body. In order to try and relax the patient, it is not uncommon for the person administering the treatment to try and laugh and chat with the patient to put them at ease. However trying to keep calming conversation going while injecting very small doses of medication can be a challenge. Administering different amounts of treatment fluid at each of the injection sites may cause the overall treatment to be less effective and may even bring some harm to the patient undergoing treatment.

SUMMARY

The injecting device disclosed herein has been developed to try and overcome this problem. The injecting device is configured to permit the person administering the treatment (hereinafter called the "user") to pre-set the desired smaller volume of a total volume of liquid medication or treatment fluid on the injecting device itself, and then to reliably deliver the exact pre-set volume to the patient. Several injections may be administered to the same patient with the injecting device without the need to change needles between each injection. The desired dosage of liquid medication or treatment fluid may be pre-set simply by pushing an arm on the housing of the injecting device with a fingertip while viewing the possible settings through an aperture provided on the housing. The user then pushes an actuator and the injecting device delivers the pre-set volume of fluid through the needle and without the user depressing a plunger. The plunger is automatically set in motion when the actuator is depressed. (The terms "drug", "medication", "liquid", "liquid medication", "fluid" and "treatment fluid" may be used interchangeably herein and should be understood to be referring to any type of fluid or liquid that may be injected into a patient.)

An injecting device includes a housing having a longitudinal axis extending. A dose setting member is rotatable in the housing in a first or second direction about the longitudinal axis. A plunger extends through a bore of the dose setting member and into a bore of a barrel engaged with the housing. Pushing on an arm extending through a slot in the housing rotates the dose setting member in the first direction. As it rotates, indicia on the dose setting member are progressively displayed through an aperture in the housing. An actuator is engaged to release the dose setting member to rotate in the second direction and this rotation causes the plunger to move axially within the barrel's bore and push the pre-set dose of fluid therefrom. The dose setting member remains in a constant axial position within the housing during rotation in each of the first and second directions.

In one aspect, the present disclosure may provide an injecting device comprising a housing having a first end and a second end, and a longitudinal axis extending between the first and second ends; wherein an interior surface of said housing bounds and defines an interior cavity; a dose setting member positioned within the interior cavity and being rotatable in one of a first direction and a second direction about the longitudinal axis; a plunger extending through a bore of the dose setting member; said plunger extending one of along the longitudinal axis and parallel to the longitudinal axis; a barrel extending outwardly from the first end of the housing and having a barrel bore adapted to hold a volume of liquid therein; wherein a tip of the plunger is received with the barrel bore and wherein rotation of the dose setting member in the second direction causes the plunger to move axially within the barrel bore; and wherein the dose setting member remains in a substantially constant axial position within the housing during rotation of the dose setting member in each of the first direction and the second direction.

In another aspect, the present disclosure may provide a method of administering a portion of a total volume of a liquid medication utilizing an injecting device, the method comprising drawing a total volume of a liquid medication into a barrel of an injecting device; determining a desired volume of total volume of the liquid medication to be injected in each of a plurality of separate injections; rotating a dose setting member of the injecting device in a first direction about a longitudinal axis of the injecting device from a first position to a second position; where the second position corresponds to a desired pre-set volume of liquid to be dispensed from the injecting device; locking the dose setting member against rotation in a second direction about the longitudinal axis; engaging an actuator provided on the injecting device; unlocking the dose setting member for rotation in the second direction; rotating the dose setting member in the second direction; drawing a feed tube axially through a bore of the dose setting member as the dose setting member rotates in the second direction; advancing a plunger extending outwardly from an end of the feed tube through a distance within a bore of the barrel; pushing the pre-set volume of liquid out of a needle engaged with the barrel; and restraining the dose setting member against axial motion during rotation of the dose setting member in the first direction and in the second direction.

The method further comprises providing a series of indicia on an exterior surface of the dose setting member; wherein the series of indicia are radially aligned with each other in a row that is oriented at right angles to the longitudinal axis; progressively displaying each of the series of indicia through an aperture defined in a housing of the injecting device within which the dose setting member rotates.

The method may further comprise displaying only one of the series of indicia at a time through the window. The advancing of the plunger occurs without pushing on a head of the plunger. The rotating of the dose setting member is accomplished by pushing an arm extending outwardly from the dose setting member in a first direction along a slot defined in the housing, wherein the slot is oriented substantially at right angles to the longitudinal axis. The method may further comprise pivoting the actuator about a pivot rod provided on the housing between an engaged position and a disengaged position; restraining the dose setting member against rotation in the second direction when the pivot rod is the engaged position; and permitting the dose setting member to rotate in the second direction when the pivot rod is in the disengaged position.

BRIEF DESCRIPTION OF THE SEVERAL VIEWS OF THE DRAWINGS

A sample embodiment of the disclosure is set forth in the following description, is shown in the drawings and is particularly and distinctly pointed out and set forth in the appended claims. The accompanying drawings, which are fully incorporated herein and constitute a part of the specification, illustrate various examples, methods, and other example embodiments of various aspects of the disclosure. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 12 is an isometric perspective view of the injecting device showing the needle thereof inserted within a bottle of fluid medication;

FIG. 13 is a longitudinal cross-section of the engagement of the plunger and the feed tube taken along line 13-13 of FIG. 12;

FIG. 23 is a longitudinal cross-section of the injecting device as shown in FIG. 22, shown in a first position; and FIG. 24 is a longitudinal cross-section of the injecting device as shown in FIG. 22, shown in a second position.

Similar numbers refer to similar parts throughout the drawings.

DETAILED DESCRIPTION

Figure 1:
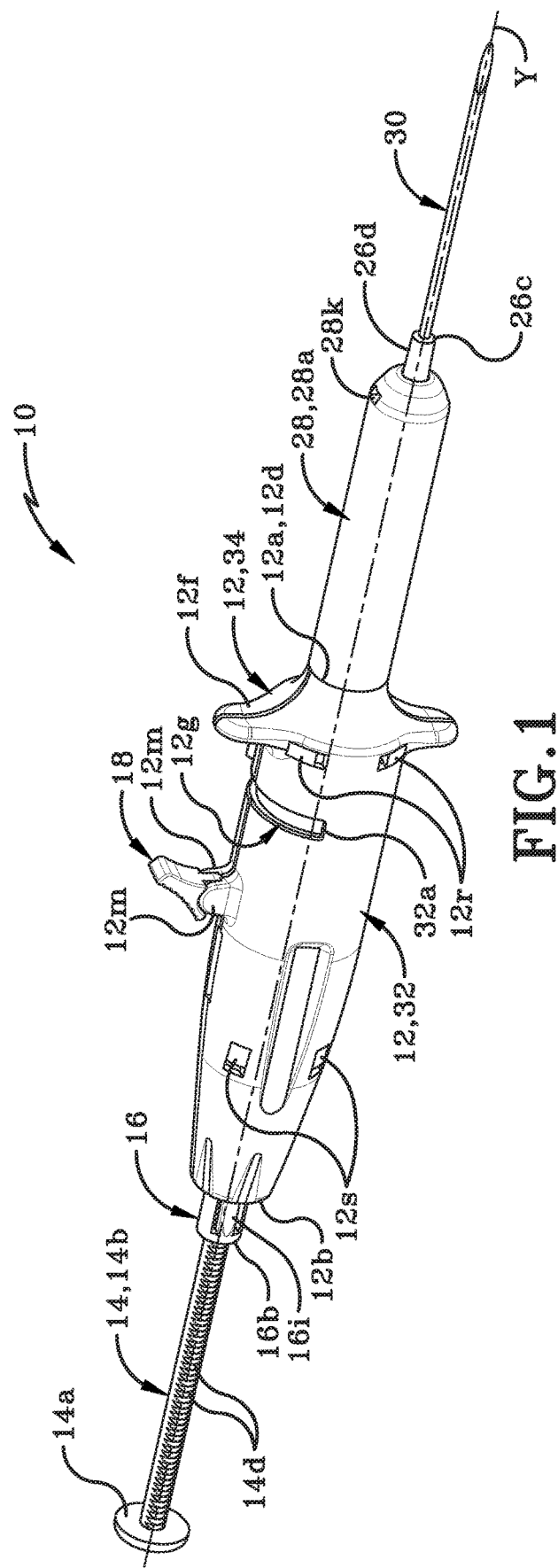
FIG. 1 is an isometric perspective view of a first embodiment of an injecting device in accordance with an aspect of the present disclosure.

Referring to FIGS. 1-16, there is shown an injecting device in accordance with an aspect of the present disclosure, generally indicated at 10. Injecting device 10 comprises a housing 12, a plunger 14, a feed tube 16, an actuator 18, a castle nut 20 (FIGS. 1A and 2), a dose setting member 22, a torsion spring 24, a barrel 26, a barrel housing 28, and a needle 30.

Figure 2:
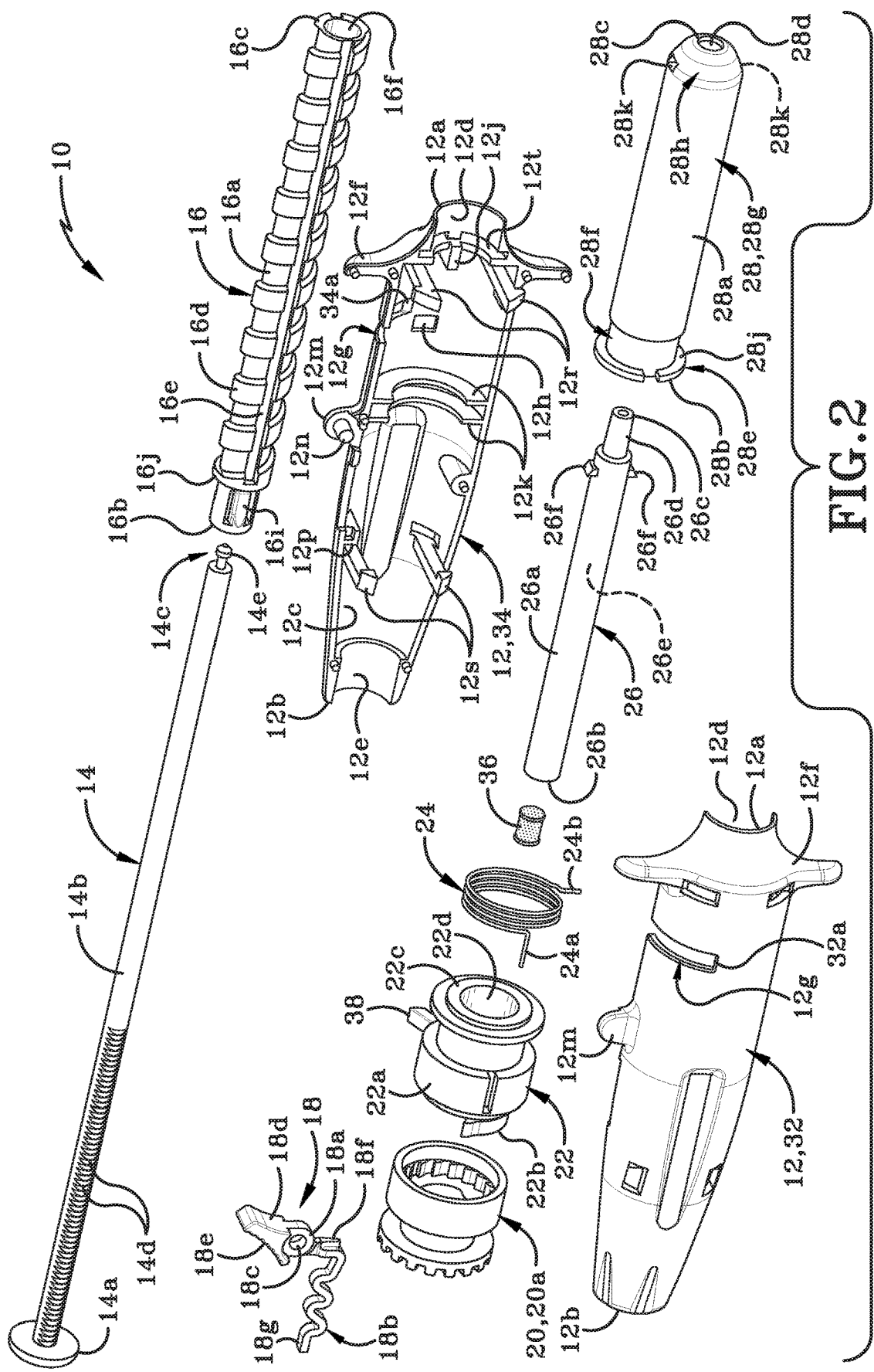
FIG. 2 is an exploded isometric perspective view of the injecting device of FIG. 1 except that the needle has been omitted therefrom.

As shown in FIG. 2, housing 12 is comprised of a first housing section 32 and a second housing section 34. First and second housing sections 32, 34 may be molded out of a suitable material, such as plastic. First and second housing sections 32, 34 are configured to be complementary to each other and are configured to be secured to each other along their outermost edges to form a longitudinally-oriented tubular member. First and second sections 32, 34 may be secured to each other in any suitable manner, such as by engaging pins provided on one or both of first and second housing sections 32, 34 into complementary recesses the other of the first and second housing sections 32, 34. In other examples, first and second housing sections 32, 34 may be secured to each other by other methods such as by heat welding.

As shown in FIG. 1, when first and second housing sections 32, 34 are secured together to form housing 12, housing 12 has a first end 12a and a second end 12b, and a longitudinal axis "Y" extends between first end 12a and second end 12b. The interior surfaces of first and second housing sections 32, 34 bound and define an interior cavity 12c (FIG. 1A) within which a number of the other component parts of injecting device 10 are fully or partially received. A first opening 12d to interior cavity 12c is defined at first end 12a and a second opening 12e to interior cavity 12c is defined at second end 12b.

A collar 12f is formed at first end 12a of housing 12. As is evident from FIG. 1, housing 12 has a tapers from a maximum diameter proximate first end 12a to a minimum diameter proximate second end 12b. In particular, collar 12f is of a greater diameter than the rest of the housing 12. Collar 12 provides a region on housing 12 that helps to ensure that when a user is gripping the housing in their hand, the user's fingers will not readily slide off first end 12a of housing 12. This may be particularly important when needle 30 is already penetrating a patient's skin as inadvertent movement of the user's hand at this point may cause injury to the patient.

Figure 1A:
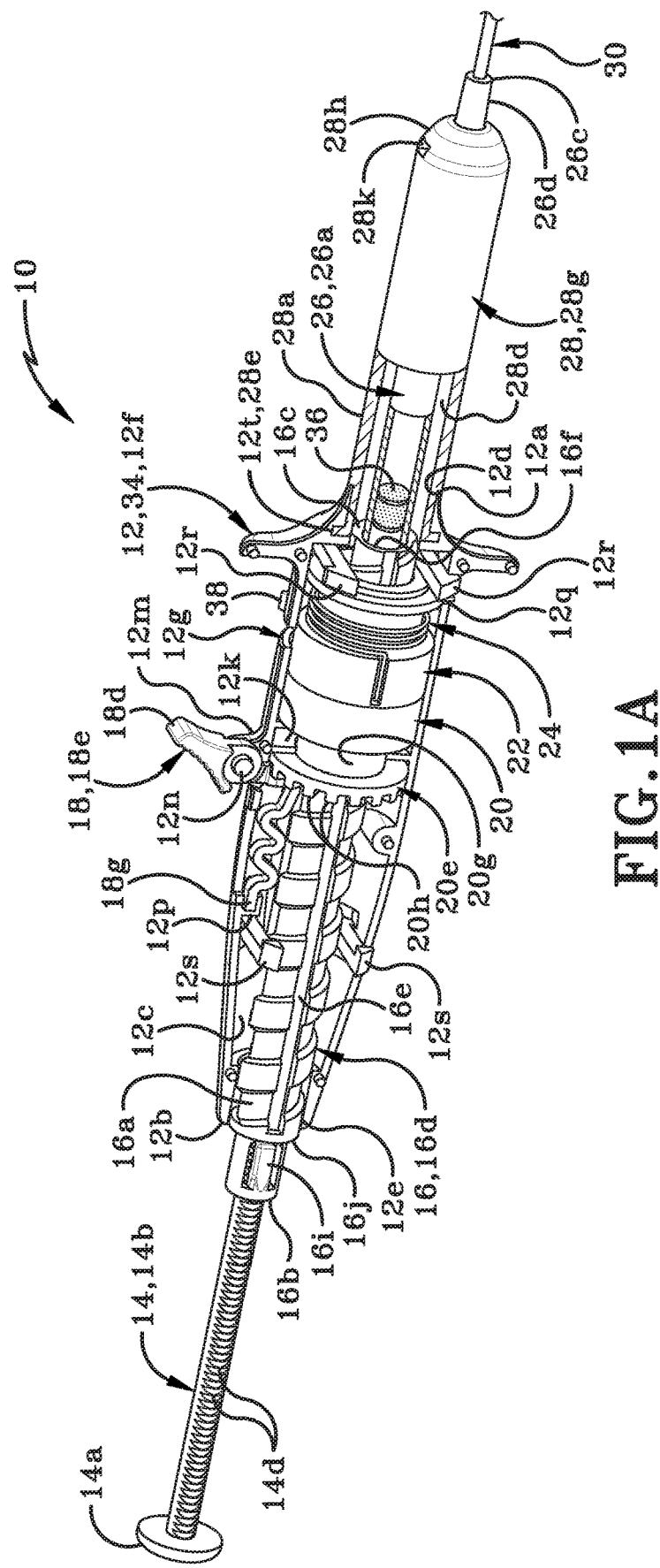
FIG. 1A is a partial isometric perspective view of the injecting device of FIG. 1 with a first housing section removed to show the interior cavity of the housing.

FIGS. 1 and 1A show that housing 12 defines an arcuate slot 12g that may be partially formed in first housing section 32 and partially formed in second housing section 34. Slot 12g is in fluid communication with interior cavity 12c in that slot 12g extends from an exterior surface of housing 12 to an interior surface thereof, where the interior surface bounds interior cavity 12c. Slot 12g extends between a first end wall 32a (FIG. 1) of first housing section 32 and a second end wall 34a (FIG. 2) of second housing section 34.

Second housing section 34 defines an aperture 12h (FIG. 2) therein that extends between the exterior surface and the interior surface of first housing section 34. Aperture 12h is in fluid communication with interior cavity 12c. Aperture 12h is located rearwardly from slot 12g (i.e., in a direction moving away from first end 12a of housing and towards second end 12b). Aperture 12h is additionally located a distance radially away from second end wall 34a of second housing section 34, i.e., a distance away from one end of slot 12g.

One or both of first housing section 32 and second housing section 34 provides a key 12j thereon. If a key 12j is provided in each of first housing section 32 and second housing section 34, these keys 12j may be laterally aligned with each other. (In other embodiments, the keys 12j may not be laterally aligned with each other.) Key 12j is provided to interlock with a complementary region provided on feed tube 16, as will be later described herein. Key 12j may comprise one of a groove and a ridge and is provided on the interior surface of the associated one of first housing section 32 and second housing section 34. As will be discussed later herein, feed tube 16 provides the other of the groove and the ridge that interlocks with key 12j.

Each of first and second housing sections 32, 34 includes a pair of annular walls 12k that extend along at least a portion of the circumferential interior surface of the associated housing section 32, 34 and into interior cavity 12c. Walls 12k walls are longitudinally spaced apart from each other and define a portion of an annular channel 12k' (FIG. 2) therebetween. The walls 12k and channel 12k' are located a distance rearwardly of aperture 12h and forwardly of key 12j. The purpose of walls 12k and channel 12k' will be described later herein.

A pair of ears 12m extends outwardly from a region of each of first housing section 32 and second housing section 34. Ears 12m are laterally aligned with each other and are located rearwardly of channel 12k'. Ears 12m may be generally in alignment with a forward end of key 12j. A pivot rod 12n (FIG. 1A) extends between the interior surfaces of ears 12m. Pivot rod 12n may extend outwardly from one of the ears 12m towards the other of the ears 12m or a first section of pivot rod 12n may extend outwardly from ear 12m of first housing section 32 and a second section of pivot rod 12n may extend outwardly from ear 12m of second housing section 34. The first and second sections of pivot rod 12n may abut each other or may interlock with each other. If first and second housing sections 32, 34 are heat welded to each other, the first and second sections of pivot rod 12n may be heat welded together to form a single pivot rod connecting the two ears 12m.

A bracket 12p (FIG. 1A) extends downwardly and inwardly from the interior surface of housing 12. A first part of the bracket 12p may be formed on first housing section 32 and a second part of bracket 12p may be formed on second housing section 34. In other instances bracket 12p may be entirely formed on one of the first and second housing sections 32, 34. The purpose of bracket 12p will be described later herein.

Housing 12 also defines a hole 12q (FIG. 1A) therein in a location rearwardly of collar 12f and forwardly of slot 12g. Hole 12q may be located a distance radially away from slot 12g. As illustrated in the attached figures, slot 12g is illustrated as being defined on an upper region of housing 12 while hole 12q is defined on a lower region of housing 12. The purpose of hole 12q will be described later herein.

It will be understood that first and second housing sections 32, 34 may be provided with a number of other structures that extend into interior cavity 12c. These other structures may help in supporting and retaining various component parts of injecting device 10 within interior cavity 12c in such a manner that will ensure these other component parts function properly. For example, first and second housing sections 32, 34 may include a plurality of connecting bars 12r and 12s that may perform at one or more different functions. Firstly, the connecting bars 12r, 12s may be utilized to help secure first and second housing sections 32, 34 to each other. Connecting bars 12r, 12s may have hooked ends that are received through openings in the opposed housing section. Secondly, connecting bars 12r, 12s may help retain certain components in set locations within interior cavity of housing 12. Connecting bars 12r are located generally in radial alignment with collar 12f, while connecting bars 12s may be located rearwardly of bracket 12p. Connecting bars 12r, 12s may be provided on one or both of first and second housing sections 32, 34 and comprise two spaced apart bars that are located vertically a distance apart from each other per the attached figures. Similarly, connecting bars 12s may include two spaced apart bars that are located vertically a distance apart from each other per the attached figures. The interior surface of first and second housing sections 32, 34 may also define an annular channel 12t that is located forwardly of collar 12f and rearwardly of the edge that defines opening 12d.

It will further be understood that various bracing or strengthening members may be provided on the exterior surface of housing 12, such as bracing members that may extend between collar 12f and the exterior surface of the wall of housing 12. Other structures and strengthening members will not be specifically identified and discussed herein.

Plunger 14 comprises a head 14a and an elongate shaft 14b that extends outwardly from head 14a and terminates at a free end 14c. Shaft 14b has a longitudinal axis that extends between head 14a and free end 14c. (The longitudinal axis of shaft 14 is parallel to and aligned with longitudinal axis "Y" when plunger 14 is engaged with housing 12.) Plunger 14 may comprise a first region, a second region, and a third region. The first region begins proximate head and may continue to approximately half-way between head 14a and free end 14c. The second region of shaft 14b begins a short distance inwardly from free end 14c and continues to approximately half-way between head 14a and free end 14c. Third region begins at free end and continues for a relatively short distance towards head 14a terminating at second end.

A plurality of ridges 14d is defined on the first region of shaft 14b. Ridges 14d are oriented at right angles to the longitudinal axis of shaft 14b and are longitudinally spaced apart from each other. Ridges 14d may be provided on a portion of the circumferential surface of shaft 14b. In particular, ridges 14d may be provided on opposed circumferentially-spaced apart side surfaces of shaft 14b. The circumferential surface of the second region of shaft 14b may be substantially smooth and free of ridges. The third region may be of a reduced diameter relative to the rest of shaft 14b. A tip 36 (FIG. 2) is fixedly engaged with free end 14c of shaft 14b. Tip 36 may be of substantially the same diameter as the rest of shaft 14b. Tip 36 may be fabricated from rubber or any other material that is capable of sealing against leaks. The purpose of tip 36 will be described later herein.

Feed tube 16 is comprises an elongate cylindrical wall 16a having a first end 16b, a second end 16c, and a longitudinal axis extending between the first and second ends 16b, 16c. (The longitudinal axis of feed tube 16 is parallel to and aligned with longitudinal axis "Y" when feed tube 16 is engaged with housing 12.) A thread 16d is provided on the exterior circumferential surface of wall 16a. Thread 16d originates a distance inwardly from first end 16b and terminates at second end 16c. In one example, thread 16d may be a helical thread.

Figure 3:
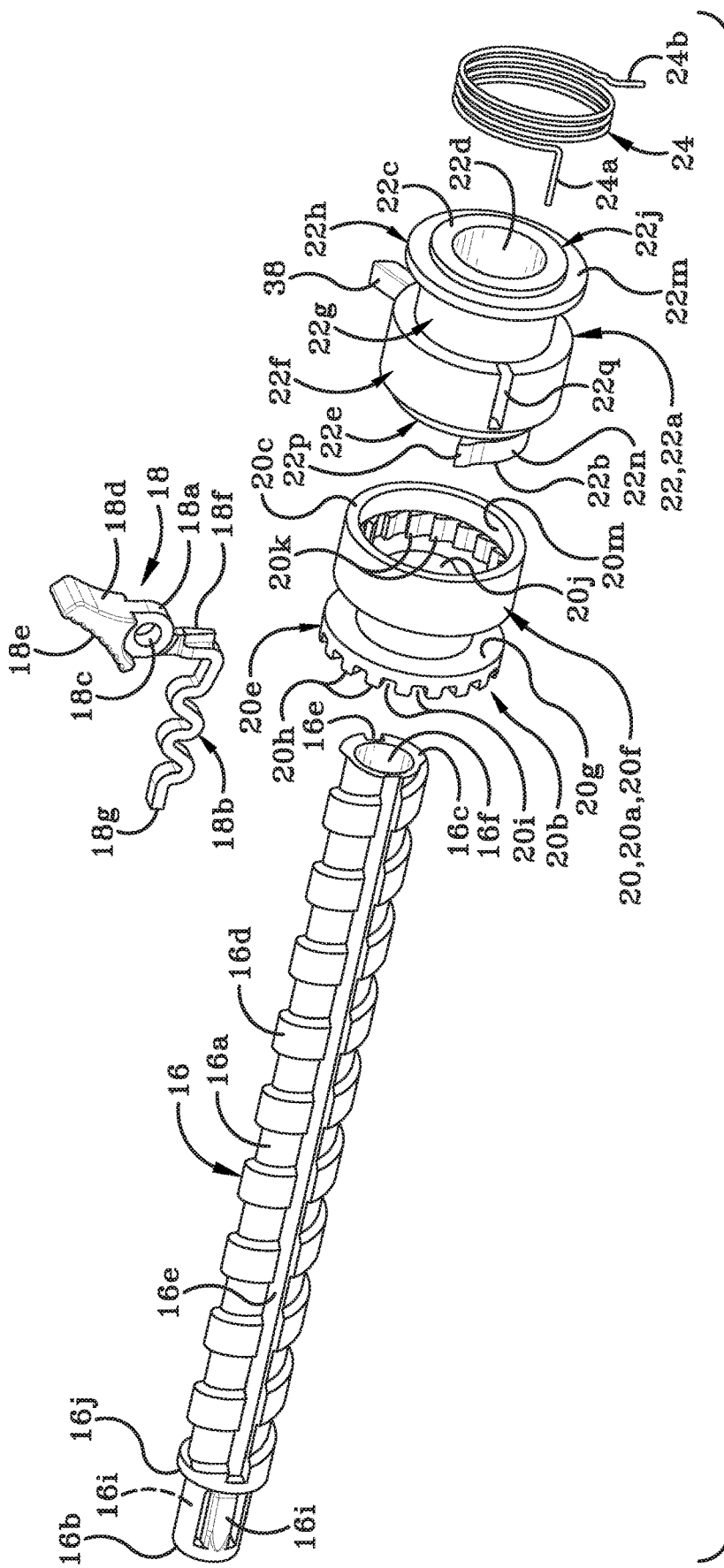
FIG. 3 is an enlarged exploded isometric perspective view of the feed tube, actuator, castle nut, dose setting member, and torsion spring.

At least one keyway 16e is provided on wall 16a. Keyway 16e is oriented substantially parallel to the longitudinal axis of wall 16a and is located so as to be complementary to the position of key 12j on housing 12. In one example, key 12j may be provided on each of the first and second housing sections 32, 34. In this instance, a complementary keyway 16e is provided on each of two spaced-apart circumferential side surfaces of feed tube 16. Keyway 16e is of a complementary structure to key 12j and is configured to be interlockingly engaged therewith. Consequently, if key 12j is provided as a groove defined in the associated one or both of first and second housing sections 32, 34, then keyway 16e may be configured as a ridge which extends outwardly from the exterior surface of wall 16a and is of a size and shape to interlockingly engage in the groove that is key 12j, and vice versa. As illustrated in the attached figures, keyway 16e is configured as a ridge. Consequently, key 12j is configured as a groove. Keyway 16e interrupts thread 16d as can be seen in FIG. 3.

Wall 16a of feed tube 16 defines a bore 16f therein that extends from an opening defined in first end 16b to an opening defined in second end 16c. Bore 16f is shaped and sized to receive a portion of shaft 14b of plunger 14 therethrough. A first region 16g of wall 16a of feed tube 16, which includes first end 16b, is of a reduced diameter relative to the rest of the wall 16a. One or more teeth 16h are provided on a flap 16i (FIG. 13) of first region 16g and these teeth 16h extend inwardly into bore 16f. If ridges 14d are provided on two sections of the circumferential surface of shaft 14b of plunger 14, then teeth 16h will be provided in complementary locations of the interior surface of first region 16g that will permit engagement between teeth 16h and ridges 14d. Teeth 16h are configured to interlock with ridges 14d of plunger 14 and thereby interlockingly engage plunger and feed tube 16 together so that they move in unison, as will be described later herein. It will be understood in other examples that the ridges on shaft 14b of plunger 14 may be oriented differently from what is illustrated in the attached figures and that teeth on the feed tube 16 will then be oriented in any manner that is complementary to the ridges to ensure interlocking engagement with the ridges. So, for example, shaft 14b may be provided with ridges that are oriented substantially parallel to longitudinal axis "Y" or at an angle of less than 90° to the longitudinal axis "Y" and the teeth on feed tube will then be oriented appropriately to interlock with the ridges.

As best seen in FIG. 2, an annular flange 16j is defined on feed tube 16 in a location between the first region that is of a smaller diameter and the rest of feed tube 16 that includes thread 16d. The smaller diameter first region is sized to extend through opening 12e defined at second end 12b of housing 12. Flange 16j may be of a diameter greater than a diameter of opening 12e. Flange 16j therefore may prevent the rest of feed tube 16 (i.e., the portion that includes threads 16d) from moving through opening 12e. Opening 12d in first end 12a of housing is of a diameter that permits the rest of feed tube 16 to pass therethrough, as will be described later herein.

Actuator 18 includes a head 18a and a tail 18b that extends outwardly from head 18a. Head 18a defines a hole 18c that extends from one side surface of head 18a to the other side surface thereof. Hole 18c is shaped and sized to receive pivot rod 12n of housing 12 therethrough. A flange 18d extends upwardly and outwardly away from head and knurling 18e (or some other textured finish or anti-slip surface) is provided on any outer surface of flange 18d. Flange 18d may be generally triangular in shape. An apex of this triangularly-shaped flange 18d is engaged with head 18a and a hypotenuse of the triangularly-shaped flange 18d is located a distance outwardly from where the apex joins head 18a. The knurling 18e is provided on the hypotenuse of the triangularly-shaped flange and is positioned to be contacted by user's fingertip or thumb.

Tail 18b of actuator 18 includes a first leg 18f that extends vertically downward from head 18a. The remaining portion of tail 18b extends rearwardly from first leg 18f and is oriented generally at right angles to first leg 18f. Tail 18b forms a series of alternating peaks and valleys, and terminates in a free end 18g. Free end 18g may be oriented generally at right angles to first leg 18f. Free end 18g is shaped and sized to be received in bracket 12p of housing 12. When a user contacts surface 18e and pushes on flange 18d to rotate head 18a about pivot rod 12n, this movement tends to compress the tail 18b of actuator 18 as the free end 18g thereof is seated in bracket 12p. Consequently, when the pushing force is removed from flange 18d, the tail 18b returns to its uncompressed state and head 18a rotates in an opposite direction and back into its original, at-rest position.

Figure 4:
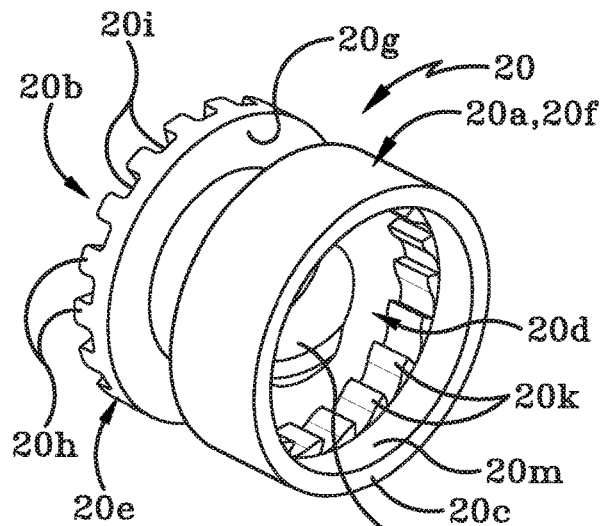
FIG. 4 is a right side perspective view of the castle nut shown on its own.
Figure 5:
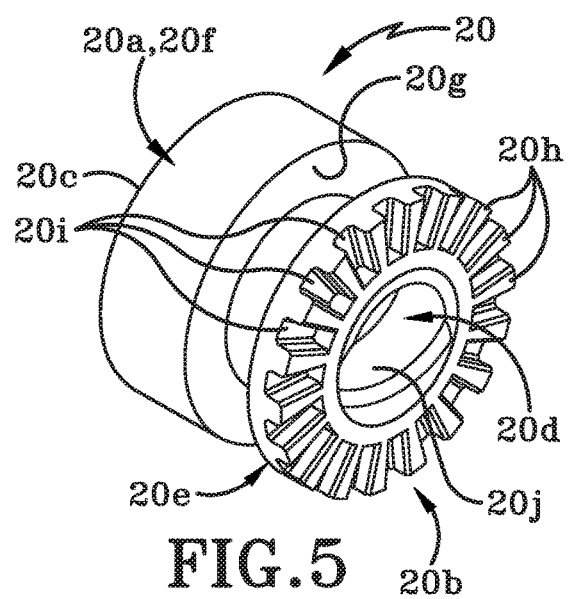
FIG. 5 is a left side perspective view of the castle nut of FIG. 4.

Castle nut 20 has an exterior wall 20a that is generally cylindrical in shape and extends from a first end 20b to a second end 20c. A bore 20d is bounded and defined by an interior surface of wall 20a. Bore 20d extends from an opening defined in first end 20b to an opening defined in second end 20c. Bore 20d is shaped and sized to receive feed tube 16 therethrough and the openings defined in each of the first end 20b and second end 20c are sized to permit feed tube 16 to travel therethrough. As best seen in FIG. 4, the size of bore 20d proximate second end 20c may be of a greater internal diameter than the diameter of bore 20d proximate first end 20b (as seen in FIG. 5). Castle nut 20 has a longitudinal axis that extends between first end 20b and second end 20c and is oriented parallel to and aligned with longitudinal axis "Y" when castle nut 20 is engaged in housing 12.

Wall 20a includes a first region 20e and a second region 20f that are separated from each other by an annular groove 20g. Groove 20g is spaced a distance inwardly from first end 20b and a distance inwardly from second end 20c. First region 20e of castle nut 20 is shaped and sized so that the first region 20e may be received within annular channel 12k' of housing 12 when castle nut 20 is received in interior cavity 12c of housing 12. In other words, the length of first region 20e (as measured from first end 20b to groove 20g) is substantially the same as the width of channel 12k' as defined between the two longitudinally spaced-apart walls 12k.

A plurality of alternating ridges 20h and valleys 20i is provided at first end 20b of castle nut 20. The ridges 20h and valleys 20i extend longitudinally outwardly from first end 20b and towards second end 12b of housing 12 when castle nut 20 is seated within interior cavity 12c. Each of the ridges 20h and valleys 20i is generally U-shaped when viewed from the side. This configuration of the ridges 20h and valleys 20i gives first end 20b the appearance of a top of a castle wall. The shape and size of each valley 20i is such that the first leg 18f of actuator 18 may be selectively received therein as will be later described herein.

As best seen in FIGS. 4 and 5, the interior surface of a portion of the castle nut 20 that defines bore 20d also defines a thread 20j therein. In particular, thread 20j is defined in the interior surface of that portion of bore 20c which extends through first region 20e. In other examples, the thread 20j is further defined in the interior surface of that portion of bore 20c which extends through the region including annular groove 20g. In one example, thread 20j is not defined in the interior surface of the portion of the bore 20d that extends through second region 20f. Thread 20j is configured to matingly engage with thread 16d on feed tube 16. In one example, thread 16d and thread 20j may be helical in nature.

Figure 10:
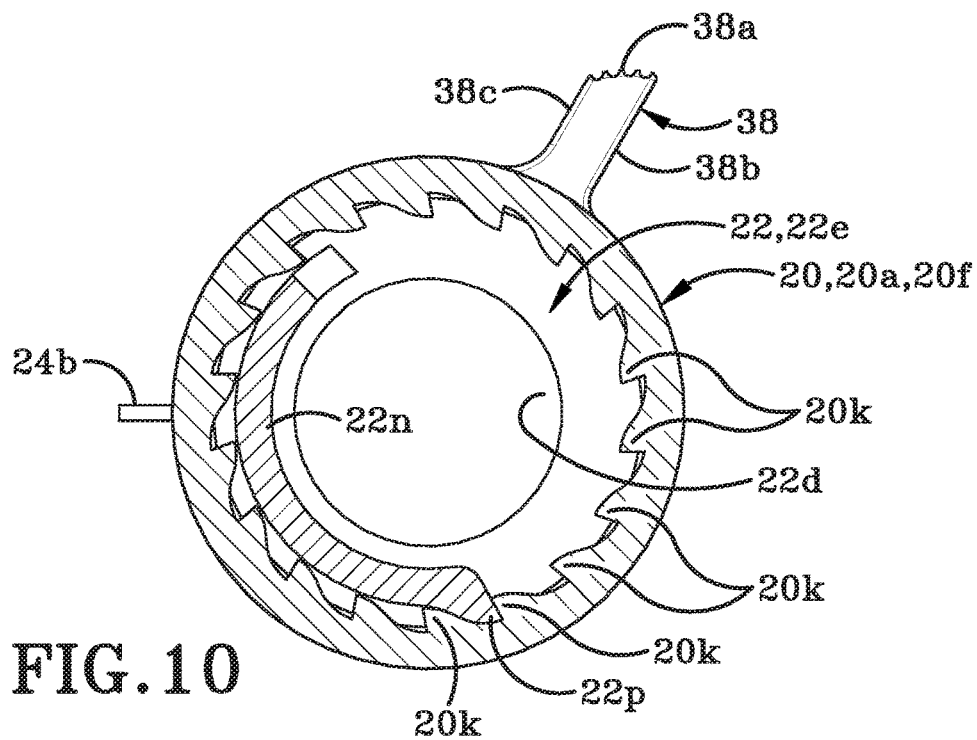
FIG. 10 is a transverse cross-sectional view of the interlockingly engaged castle nut and dose setting member taken along line 10-10 of FIG. 9.

As best seen in FIGS. 4 and 10, an annular ring of gear teeth 20k is defined in the interior surface of bore 20c that extends through second region 20f of castle nut 20. Gear teeth 20k extend inwardly into bore 20c and the valleys defined between adjacent gear teeth 20k may be generally oriented parallel to the longitudinal axis of castle nut 20. As can be seen best in FIG. 4, the annular ring of gear teeth 20k is located a distance inwardly away from second end 20c so that a smooth section 20m extends between gear teeth 20k and second end 20c.

Figure 6:
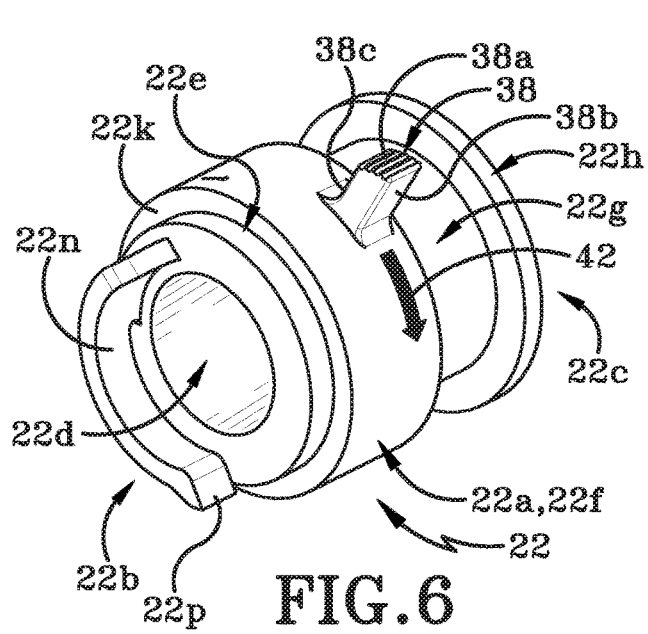
FIG. 6 is a left side perspective view of the dose setting member shown on its own.
Figure 7:
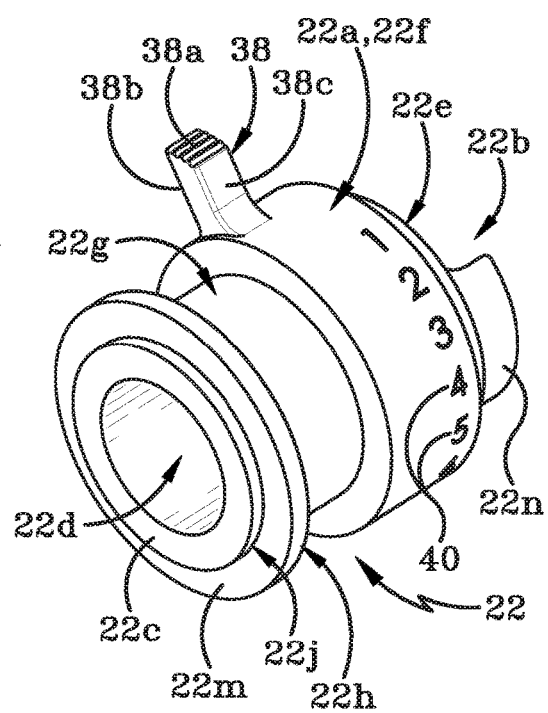
FIG. 7 is a right side perspective view of the dose setting member of FIG. 6.

Dose setting member 22 is shown in greater detail in FIGS. 6 and 7. Dose setting member 22 has an exterior wall 22a that is generally cylindrical in shape and extends from a first end 22b to a second end 22c. A bore 22d is defined by an interior surface of wall 22a and bore 22d extends from an opening defined in first end 22b to an opening defined in second end 22c. Bore 22d is shaped and sized to receive feed tube 16 therein and the openings in first end 22b and second end 22c are shaped and sized to permit feed tube 16 to travel therethrough. Dose setting member 22 has a longitudinal axis that extends between first end 22b and second end 22c and is oriented parallel to and aligned with longitudinal axis "Y" when dose setting member 22 is engaged in housing 12.

Wall 22a of dose setting member 22 may be configured into five distinct annular regions that are of different external diameters from each other. As illustrated, wall 22a is configured into a first region 22e, a second region 22f, and a third region 22g, a fourth region 22h, and a fifth region 22j. First region 22e is configured to be complementary in shape and size to be received within the larger diameter region of bore 20d of castle nut 20, i.e., in the larger diameter bore 20d proximate second end 20c of castle nut 20. In particular, first region 22e has an external diameter that is substantially the same as the interior diameter of smooth section 20m of castle nut 20. Second region 22f of dose setting member 22 has an external diameter that is greater than the external diameter of first region 22e. As a consequence, second region 22f cannot be received into the bore 20d of castle nut 20 proximate second end 20c. Furthermore, a portion of second region 22f extends radially outwardly beyond the exterior surface of first region 22e and forms a shoulder 20k. Shoulder 20k abuts second end 20c of castle nut 20 when first region 22f of dose setting member 22 is inserted into bore 20d of castle nut 20 at second end 20c.

Third region 22g of dose setting member 22 has an external diameter that is smaller than the external diameter of second region 22f. In one example, the external diameter of third region 22g may be substantially the same as the external diameter of first region 22e. Fourth region 22h of dose setting member 22 has an external diameter that is greater than the external diameter of third region 22g. In one example, the external diameter of the fourth region 22h may be substantially the same as the external diameter of second region 22f. Fifth region 22g has an external diameter that is less than the external diameter of fourth region 22h. In one example, the external diameter of fifth region 22g may be substantially the same as the external diameter of either of first region 22e or third region 22g. A portion of fourth region 22f extends outwardly beyond the exterior surface of fifth region 22g and forms a shoulder 22m. The purpose of shoulder 22m will be discussed later herein.

Figure 11:
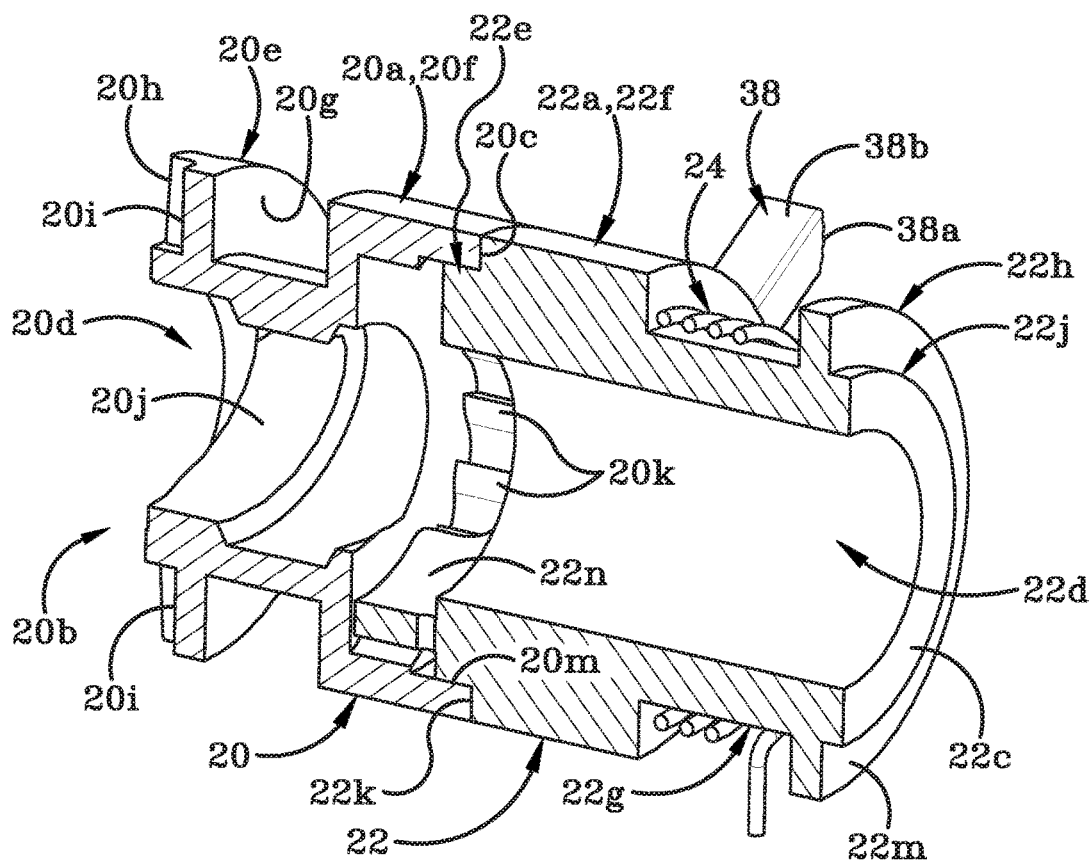
FIG. 11 is a longitudinal cross-sectional view of the interlockingly engaged castle nut and dose setting member taken along line 11-11 of FIG. 9.
Figure 11A:
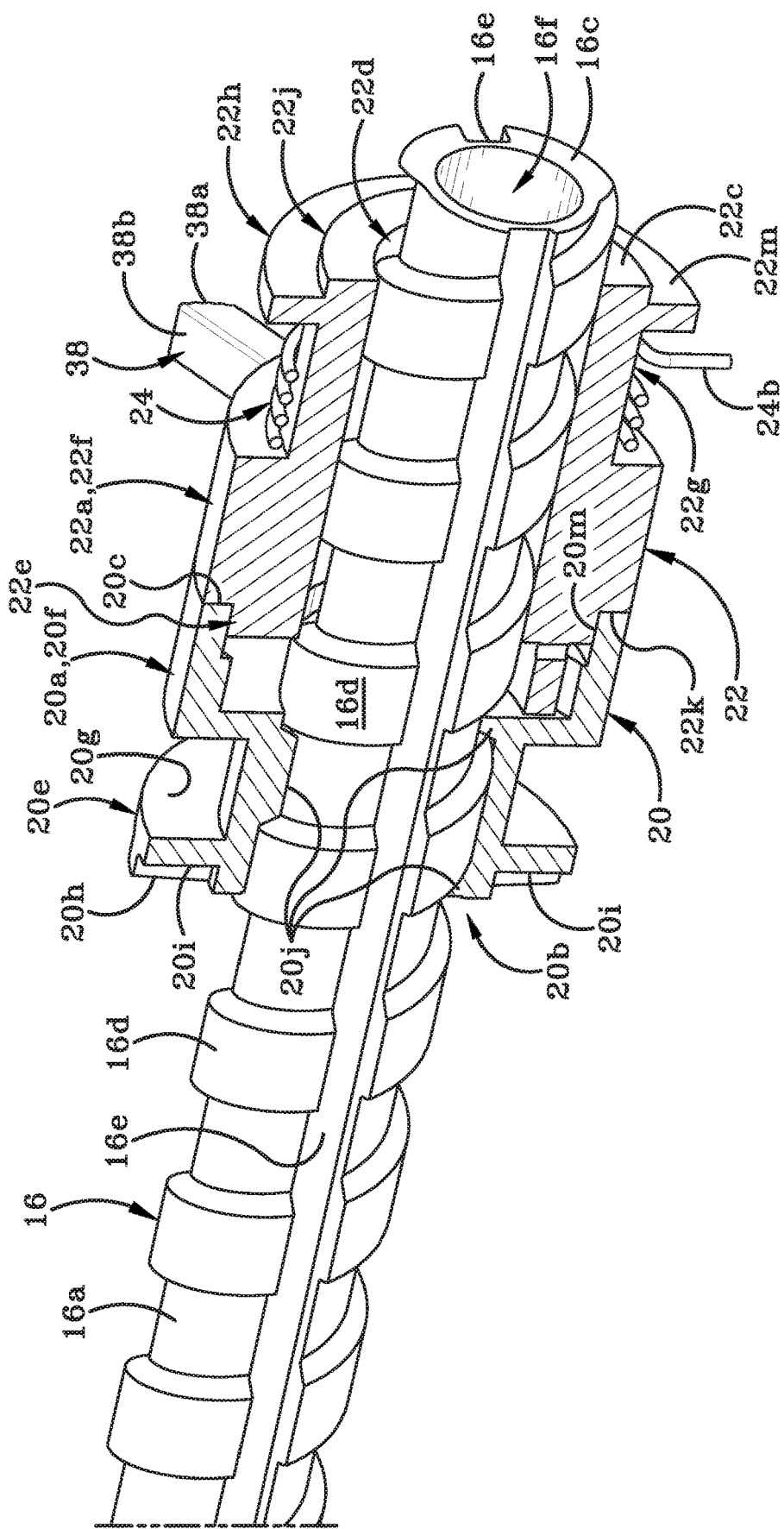
FIG. 11A is a longitudinal cross-sectional view of the interlockingly engaged castle nut and dose setting member with the feed tube engaged therewith.

An arcuate flange 22n extends longitudinally outwardly from first end 20b of first region 22e. Flange 22n is located a distance radially outwardly away from the edge of the interior surface of dose setting member 22 that defines the opening to bore 22d. Flange 22n is also located a distance radially inwardly away from the exterior surface of first region 22f of dose setting member 22. Flange 22n is may be substantially C-shaped when dose setting member 22 is viewed from one end. As best seen in FIG. 11, one end of arcuate flange 22n may be shaped into an angular tip 22p that is configured to be able to interlocking engage between adjacent gear teeth 20k on castle nut 20 when dose setting member 22 is engaged with castle nut 20.

When castle nut 20 and dose setting member 22 are engaged with each other, first region 22e of dose setting member 22 is inserted through the opening defined in second end 20c of castle nut 20 and into the bore 20d. Dose setting member 22 is pushed inwardly toward first end 20b of castle nut 20 until tip 22p of arcuate flange 22n is located in alignment with the row of gear teeth 20k. At this point, the exterior surface of first region 22e of dose setting member 22 is located inwardly and adjacent to the interior surface of second region 20*f* of castle nut 20 that defines bore 20*d*. Second end 20*c* of castle nut 20 abuts shoulder 22*k* of second region 22*f* of dose setting member 22. This interlocking engagement is illustrated in FIG. 10.

As indicated earlier herein, dose setting member 22 and castle nut 20 are retained in engagement with each other by way of a geared connection. It should be noted from FIG. 11 that the gear teeth 20*k* of castle nut 20 are oriented so that when dose setting member 22 is rotated in a first direction about longitudinal axis "Y", the tip 22*p* of flange 22*k* may readily ride over gear teeth 20*k*. This arrangement permits dose setting member 22 to rotate independently from and relative to castle nut 20. However, when dose setting member 22 is rotated in a second direction (opposite to the first direction), the tip 22*p* of flange 22*k* becomes wedged between two adjacent gear teeth 20*k* in the row of gear teeth 20*k*. This interlocking engagement between gear teeth 20*k* and tip 22*p* interlockingly engages dose setting member 22 and castle nut 20 together to a sufficient degree that castle nut 20 will rotate in unison with dose setting member 22 in the second direction.

It will be understood that instead of the gear teeth being provided on castle nut 20 and the flange with the tip that engages in the gear teeth being provided on the dose setting member 22, in other examples the gear teeth may be provided on the dose setting member 22 and the flange with the tip that engages selectively in the gear teeth may be provided on the castle nut. It will further be understood that any other manner of restricting and permitting the rotational motion of the dose setting member about the longitudinal axis and in the second direction may be utilized instead of the disclosed geared connection between the castle nut and the dose setting member.

When the engaged castle nut 20 and dose setting member 22 are installed in interior cavity 12*c* of housing 12, first region 20*e* of castle nut 20 is received within channel 12*k'* as previously mentioned herein. Shoulder 22*m* of fourth region 22*h* of dose setting member 22 is placed in abutting contact with or in close proximity to a rearward-facing surface of the connecting bars 12*r* of housing 12. Fifth region 20*j* of dose setting member 22 is sized to be positioned between the interior surfaces of the two opposing connecting bars 12*r*. This can best be seen in FIG. 1A. The walls 12*k* that define annular channel 12*k'* and the connecting bars 12*r* substantially restrain the castle nut 20 and dose setting member 22 against axial motion, i.e., motion along longitudinal axis "Y". The engaged castle nut 20 and dose setting member 22 are, however, able to rotate around longitudinal axis "Y" while being positioned between walls 12*k* and connecting bars 12*r*.

Figure 8:
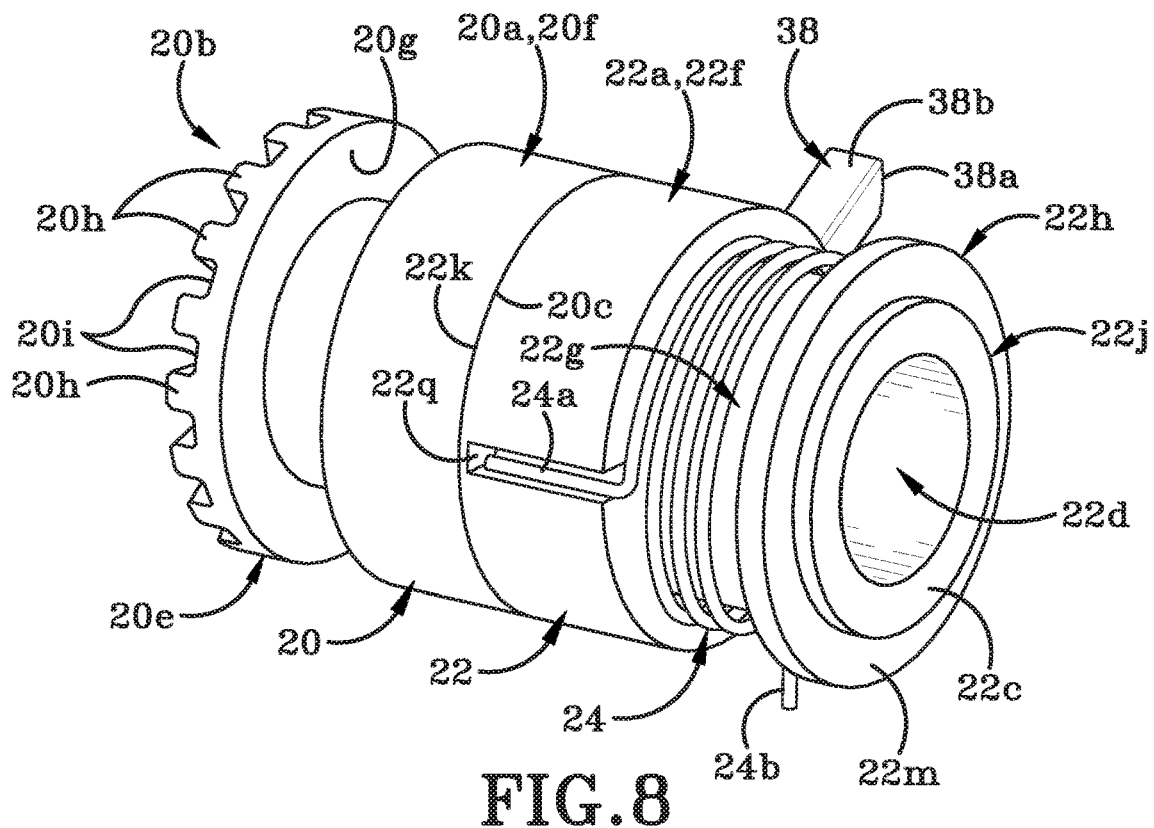
FIG. 8 is an isometric perspective view of the castle nut and dose setting member interlockingly engaged with each other.
Figure 9:
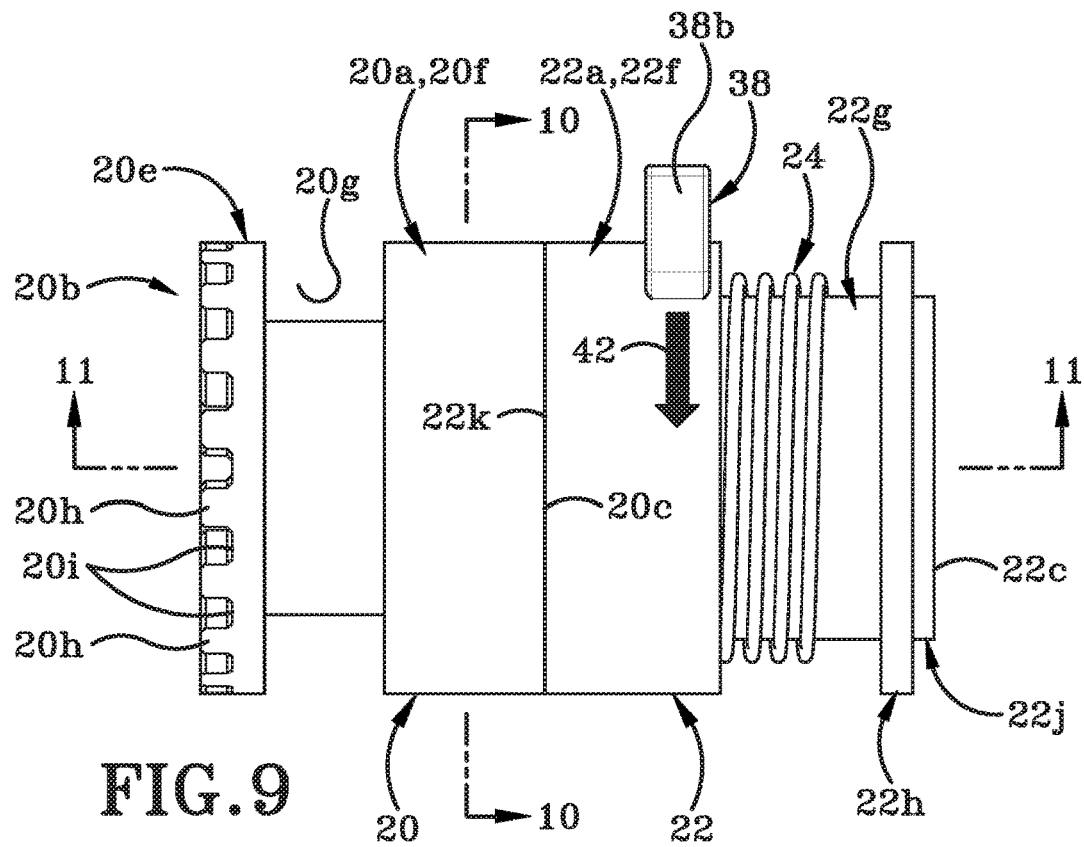
FIG. 9 is a front elevation view of the interlockingly engaged castle nut and dose setting member of FIG. 8.

Referring now to FIGS. 6, 7, and 8, second region 22*f* of dose setting member 22 includes an arm 38 that extends radially outwardly from second region 22*f*. Arm 38 may be integrally formed with second region 22*f* or may be independently fabricated and secured thereto. An end face 38*a* of arm is angled relative to the exterior surface of section region 22*f* and may be provided with knurling or some other textured or anti-slip surface thereon. A first side 38*b* and a second side 38*c* of arm 38 may extend outwardly from the exterior surface of second region 22*f* and may be ergonomically-shaped and made long enough to be manipulated by a user of injecting device 10.

Arm 38 is positioned on second region 22*f* in a location that will align with the slot 12*g* in housing 12. When dose setting member 22 is located within interior cavity 12*c* of housing 12, arm 38 will protrude outwardly through slot 12*g* and for a distance beyond the exterior surface of the housing wall. Arm 38 is of a sufficient length to ensure a user can readily and easily push on the portion of arm 38 that extends through slot 12*g* in order to set a dose of fluid or fluid medication to be delivered by injecting device 10. When a user does use a fingertip or thumb to push on arm 38, arm 38 will travel along slot 12*g* in housing 12 from first end wall 34*a* and towards first end wall 32*a* as dose setting member 22 rotates within interior cavity 12*c* in a first direction. This will be described later herein. It will be understood that when dose setting member 22 rotates in a second direction, arm 38 will travel along slot from first end wall 32*a* towards first end wall 34*a*.

Still referring to FIGS. 6 to 8, second region 22*f* is also provided with a plurality of indicia 40 on its exterior surface. Indicia 40 are provided to indicate units of fluid or fluid medication to be delivered by injecting device 10. Indicia 40 may be one of stamped, printed, etched, and applied in any other suitable manner to the exterior surface of second region 22*f*. Indicia 40 may be provided a distance circumferentially away from second side 38*c* of arm 38. Indicia 40 are spaced apart at regular intervals from each other and are arranged in a single row that is oriented at right angles to the longitudinal axis of dose setting member 22. In other words, indicia 40 are radially aligned with each in a row that is oriented at right angles to the longitudinal axis "Y" of injecting device 10 when assembled. Indicia 40 are located so as to be able to be separately and individually brought into alignment with the aperture 12*h* defined in second housing section 34.

It will be understood that each indicia 40 in the row of indicia 40 represents one unit of a dose of fluid medication to be delivered by injecting device 10. Any suitable unit measurement may be represented by indicia 40. Indicia 40 may, for example, comprise a sequential series of whole numbers such as the numbers 1, 2, 3, 4, 5, and 6 as illustrated in the attached figures. A sequential series of numbers such as 0.1, 0.2, 0.3 etc. may alternatively be utilized as indicia 40. It will further be understood that any other desired type of indicia 40 may be utilized instead of the numbers illustrated in the attached figures.

In an at-rest position, i.e., when dose setting member 22 is not actively being engaged to set a dose of medication, a portion of the exterior surface of second region 22*f* is visible through aperture 12*h* in housing 12, but the portion of the exterior surface is free of any indicia 40. In other words, no unit of measurement is displayed through aperture 12*h*; just a blank piece of wall 22*a* is visible through aperture 12*h*. It is therefore clear to the user that no dosage unit has been set. When a user pushes on arm 38 and rotates dose setting member 22 about longitudinal axis "Y" in a first direction (as will be described in detail later herein), the indicia 40 sequentially will come into alignment with aperture 12*h*. Aperture 12*h* is sized so that only one, single indicia 40 will be visible through aperture 12*h* at any one time. For example, if the dose setting member 22 is rotated to so that the number "3" is visible through the aperture 12*h*, then the injecting device 10 is loaded to deliver a medication dose of three units to a patient. The rest of the indicia 40, i.e., the numbers 1, 2, 4, 5, and 6 will not be visible to the user through aperture 12*h*. If the dose setting member 22 is rotated so that the number "6" is visible through aperture 12*h*, then the injecting device 10 is located to deliver a medication dose of six units to the patient. The rest of the indicia 40, i.e., the numbers 1, 2, 3, 4, and 5 will not be visible to the user. It will be understood that the numbers 1, 2, 3, 4, 5, and 6 are provided on the figures by way of illustration only. Fewer than six units may be represented by indicia 40 on second region 22f and more than six units may be represented by indicia 40 on second region 22f. Only a single aperture 12h is available on housing 12 to display indicia 40.

It will be understood that in other examples, the indicia may be marked directly onto the exterior surface of housing 12 and some type of indicator (such as a line or arrow for example) may be provided on the exterior surface of the dose setting member 22 and be visible through aperture 12h. Then when the line or arrow aligns with a particular one of the indicia on the exterior surface of the housing 12, then the user will know the medication dose that the injecting device 10 is set to deliver.

Referring to FIG. 6, it can be seen that second region 22f of dose setting member 22 may also include a direction marker 42. The direction marker 42 is shown as an arrow in the attached figures but it will be understood that any other representation may be used instead of the arrow. For example the words "push up" may be utilized instead of the arrow. Direction marker 42 is provided to indicate to a user which direction to move arm 38 along slot 12g in order to set a specific number of units as a dosage size for delivery to the patient. The direction marker 42 may be radially aligned with arm 38 and may be located so as to be clearly visible through slot 12g in housing 12. Direction marker 42 may also be located on the opposite side of arm 38 from indicia 40.

In one examples another opening in addition to slot 12g may be provided in housing 12 for display of the direction marker 42. In this instance, direction marker 42 will be located on dose setting member 22 in any suitable location that brings direction marker and this other opening into alignment. In other examples, direction marker 42 may be provided on the exterior surface of housing 12 and be visible at all times. Direction marker 42 may comprise both wording and an image so that the user clearly understands how to set the dosage of medication to be delivered.

Referring to FIGS. 1 and 8, second region 22f of dose setting member 22 defines a slot 22q therein. Slot 22q originates in an edge of second region 22f that is proximate to third region 22g and extends longitudinally toward the edge of second region 22f that is proximate to first region 22e. Slot 22q may terminate prior to reaching the edge of second region 22f that is proximate to first region 22e. Slot 22q is not in fluid communication with bore 22d of dose setting member 22 but, instead, terminates a distance radially outwardly away from bore 22d. The purpose of slot 22q will be described later herein.

FIGS. 3 and 8-10 show torsion spring 24 in greater detail. Torsion spring 24 is configured to be placed around the exterior surface of third region 22g of dose setting member 22. Torsion spring 24 is comprised of a plurality of coils and has a first end 24a and second end 24b. First end 24a extends outwardly from the plurality of coils and is oriented at generally at right angles thereto. First end 24a is placed into and retained within slot 22q of second member 22f and thereby interlockingly engages torsion spring 24 to dose setting member 22. Second end 24b of torsion spring 24 extends radially outwardly from an opposite region of the plurality of coils. Second end 24b is inserted through hole 12q defined in housing 12 and thus engages torsion spring 24 to housing 12.

When dose setting member 22 is rotated in the first direction to set the injecting device to deliver a pre-determinate dose of liquid medication, torsion spring 24 is caused to move from an at-rest position and become more tightly wound around third region 22g because first end 24a of torsion spring 24 is engaged with dose setting member 22 and second end 24b of torsion spring 24 is engaged with housing 12. Consequently, rotating dose setting member 22 in the first direction causes torsion spring 24 to store up energy. When injecting device 10 is activated to deliver a dose of medication as will be discussed later herein, torsion spring 24 is no longer restrained in its tightly coiled position and therefore uses the stored up energy to move back from its tightly wound condition back to its at-rest position. As torsion spring 24 returns to the at-rest position, the spring causes dose setting member 22 to rotate in a second direction about longitudinal axis "Y".

Referring to FIG. 2, barrel 26 comprises a wall 26a with a first end 26b and a second end 26c. Barrel 26 has a longitudinal axis that extends between first end 26b and second end 26c. (The longitudinal axis of barrel 26 is parallel to and aligned with longitudinal axis "Y" when barrel 26 is engaged with housing 12.) Barrel 26 includes a needle hub 26d that includes second end 26c. Needle hub 26d progressively increases in diameter from second end 26c to a location spaced a distance rearwardly from second end 26c. (In other words, needle hub 26d tapers towards second end 26c.) Barrel 26 defines a bore 26e (FIG. 14) therein that extends from an opening in first end 26b to an opening in second end 26c. Bore 26e is of an internal diameter that is substantially identical to tip 36 of plunger 14. Tip 36 and a portion of shaft 14b of plunger 14 are receivable within bore 26e and are movable longitudinally in a first direction to draw a volume of liquid medication 48 (FIG. 14) into bore 26e, and in a second direction to push liquid medication from bore 26e as will be described later herein.

Still referring to FIG. 2, one or more flanges 26f extend radially outwardly from an exterior surface of wall 26a of barrel 26. The one or more flanges 26f are located a distance rearwardly of needle hub 26d. The purpose of flanges 26f will be explained later herein.

Barrel housing 28 comprises a wall 28a with a first end 28b and a second end 28c. Barrel housing 28 has a longitudinal axis that extends between first end 28b and second end 28c. (The longitudinal axis of barrel housing 28 is parallel to and aligned with longitudinal axis "Y" when barrel housing 28 is engaged with housing 12.) Barrel housing 28 defines a bore 28d therein that extends from an opening in first end 28b to an opening in second end 28c. Bore 28d has an internal diameter that is sized to receive second end 16c of feed tube 16 therein, as will be later described herein. The opening in second end 28c is of a shape and size suitable to receive needle hub 26d of barrel 26 therethrough but is too small to permit the rest of barrel 26 to pass therethrough.

Wall 28a includes a first region 28e, a second region 28f, a third region 28g, and a fourth region 28h that are aligned longitudinally but are of different external diameters. First region 28e is of a first diameter and includes first end 28b and a shoulder 28j that is located a distance inwardly from first end. Second region 28f extends longitudinally outwardly from a portion of first region 28e that is remote from first end 28b. Second region 28f is of a smaller diameter than the diameter of first region and shoulder 28j of first region 28e extends radially outwardly beyond an exterior surface of second region 28f. Third region 28g extends outwardly from second region 28f and is located between second region 28f and fourth region 28h. Third region 28g is of a greater diameter than second region 28f but is of a lesser diameter than first region 28e. Fourth region 28h extends outwardly from third region 28g and includes second end 28c. Fourth region 28h progressively tapers in diameter from the diameter of third region 28g to a smaller diameter at second end 28c. When barrel 26 is received within bore 28d, needle hub 26d of barrel 26 extends outwardly from fourth region 28h and particularly from second end 28c.

As best seen in FIG. 1A, wall 28a of barrel housing 28 defines one or more radial openings 28k therein. Openings 28k may be located in third region 28g or in fourth region 28h and are located so as to receive the one or more flanges 26f of barrel 26 therethrough. Barrel 26 is inserted into bore 28d of barrel housing 28 and is pushed forwardly toward second end 28c of barrel housing 28 until needle hub 26d protrudes outwardly through the opening in second end 28c. Barrel 26 is further pushed forwards towards second end 28c until flanges 26f come into alignment with openings 28k and snap-fit into the same. When flanges 26f are engaged in openings 28k, barrel 26 and barrel housing 28 are interlockingly engaged with each other and substantially form a unitary component. After barrel 26 and barrel housing 28 have been so engaged, a hollow needle 30 (FIG. 1) may be selectively engaged with needle hub 26d.

When barrel housing 28 is engaged with first and second housing sections 32, 34, first region 28e of barrel housing 28 is received within annular channel 12t of housing 12. The edge of first and second housing sections 32, 34 that defines opening 12d at first end 12a of housing 12 will abut or be located in close proximity to the exterior surface of third region 28g of barrel housing 28. Barrel housing 28 and the barrel 26 engaged therewith therefore will protrude through opening 12d and extend outwardly and forwardly from first end 12a of housing 12.

It should be noted that wall 28a of barrel housing 28 may be fabricated out of a transparent material so that the contents of barrel 26 may be visible therethrough to the user of injecting device 10. Measurement graduations 44 (FIGS. 14-16) may be provided on wall 28a of barrel housing 28 or on wall 26a of barrel 26. In one example, barrel housing 28 may alternatively be provided with a window that is in fluid communication with bore 28e and through which graduations 44 may be seen. In either event, graduations 44 are located so as to be readily visible to the user. The graduations 44 may be utilized to indicate or measure the volume of liquid retained within barrel 26.

Injecting device 10 is assembled as follows. The components may be selectively engaged with each other by positioning at least one component in one of the first and second housing sections 32, 34 and then progressively engaging the other components therewith. Alternatively, the components may be engaged with each other and once engaged they may be positioned in the appropriate locations within first and second housing sections 32, 34. The following description is directed to the first scenario.

Castle nut 20 and dose setting member 22 may be engaged with each other as described earlier herein so that, together, they form a substantially unitary component. Torsion spring 24 may be placed around third region 22g of dose setting member 22 and first end 24a of torsion spring 24 may be placed in slot 22q of second region 22f of dose setting member 22. The engaged castle nut 20 and dose setting member may then be positioned within second housing section 34 by inserting second end of torsion spring 24 within hole 12t and inserting first region 20e of castle nut 20 into annular channel 12k'. Shoulder 22m of dose setting member 22 is placed in contact with connecting bars 12r in such a way that arm 38 on dose setting member 22 is positioned to extend through slot 12g of second housing section 34. The interlocked castle nut 20 and dose setting member 22 are then pushed inwardly toward the interior surface of second housing section 34 until they snap-fit into place.

Plunger 14 is inserted through bore 16f of feed tube 16 so that free end 14c of plunger extends outwardly beyond second end 16c of feed tube 16 and so that teeth 16h of feed tube 16 engage with ridges 14d on plunger 14. Keyway 16e on feed tube 16 is engaged with key 12j on second housing section 34 and free end 14c of plunger and second end 16c of feed tube 16 are inserted into bore 20d of castle nut 20. Plunger 14 and feed tube 16 are moved forwardly into bore 20d and may be rotated slightly to ensure that threads 16d on feed tube 16 engage with threads 20j of castle nut 20. A portion of feed tube 16 may extend through bore 22d of dose setting member 22 and a length of feed tube and/or a length of plunger 14 including free end 14c, may extend out of bore 22d and beyond second end 22c of dose setting member 22. Tip 36 is engaged on free end 14c of plunger 14. Feed tube 16 may be snap-fitted between connecting bars 12s on second housing section 34.

Barrel 26 is inserted into bore 28d of barrel housing 28 and is pushed forwardly therethrough toward second end 28c until flanges 26f on barrel 26 extend through openings 28k on barrel housing 28. First region 28e of barrel housing 28 is engaged in annular channel 12t of second housing section 34.

Head 18a of actuator 18 is engaged with ear 12m on second housing section 34 by aligning hole 18c on actuator 18 with pivot rod 12n on second housing section 34 and pushing head 18a onto pivot rod 12n. Free end 18g of actuator 18 is inserted into bracket 12p on second housing section 34. First leg 18f of actuator 18 is positioned within one of the valleys 20i of castle nut 20.

First housing section 32 is then secured to second housing section 34 by aligning complementary regions of the two housing sections with each other and pressing the housing sections together. As previously described herein, other methods may be used to secure first and second housing sections 32, 34 to each other. Hollow needle 30 is engaged with needle hub 26d of barrel 26 when injecting device 10 is about to be used to administer a fluid medication to a patient.

Injecting device 10 is used to administer a dose of fluid medication in the following way. The user will first engage needle 30 in needle hub 26d and will then insert the tip of needle 30 into a bottle of liquid medication 46. The user will pull the plunger 14 rearwardly away from the housing 12 in the direction indicated by arrow "A" (FIG. 12). The rearward movement of plunger 14 causes tip 36 of plunger 14 to move rearwardly within bore 26e of barrel 26 creating a vacuum therein. This in turn will cause medication 48 to be drawn out of bottle of medication 46 and into bore 26e of barrel 26. Needle 30 is withdrawn from bottle 46 and plunger 14 may then be manually pushed inwardly toward housing 12 (i.e., in the opposite direction to arrow "A") to a small extent to push any air out of needle 30. It should be noted that when a volume of medication 48 is drawn into bore 26e of barrel 26, the total volume of medication 48 to be injected into a particular patient will be drawn into bore 26e. However, that total volume of medication 48 will be administered to the patient in the form of a plurality of injections of smaller volumes of medication. For example, 100 ccs of medication 48 may be withdrawn from medication bottle 46 but only 10 ccs of medication 48 may be administered to the patient with each separate injection. So, if the total volume of medication to be administered to the patient and each pre-set dose is 10 cc, then the total volume of 100 cc will be administered to the patient through ten separate injections. The stated volumes of medication should be considered to be exemplary only and should not in any way be considered to limit the scope of the present disclosure.

It should also be noted, referring to FIG. 13, when plunger 14 is withdrawn in the direction of arrow "A", the ridges 14d on plunger 14 will causes the first region of feed tube 16 that includes teeth 16h to flex inwardly and outwardly as ridges 14d slide past teeth 16h. The inwardly and outwardly flexing motion is indicated by arrows "A1". Plunger 14 slides along longitudinal axis "Y" relative to feed tube 16 and out of the bore 16c thereof but engagement between plunger 14 and feed tube 16 is maintained.

Figure 15:
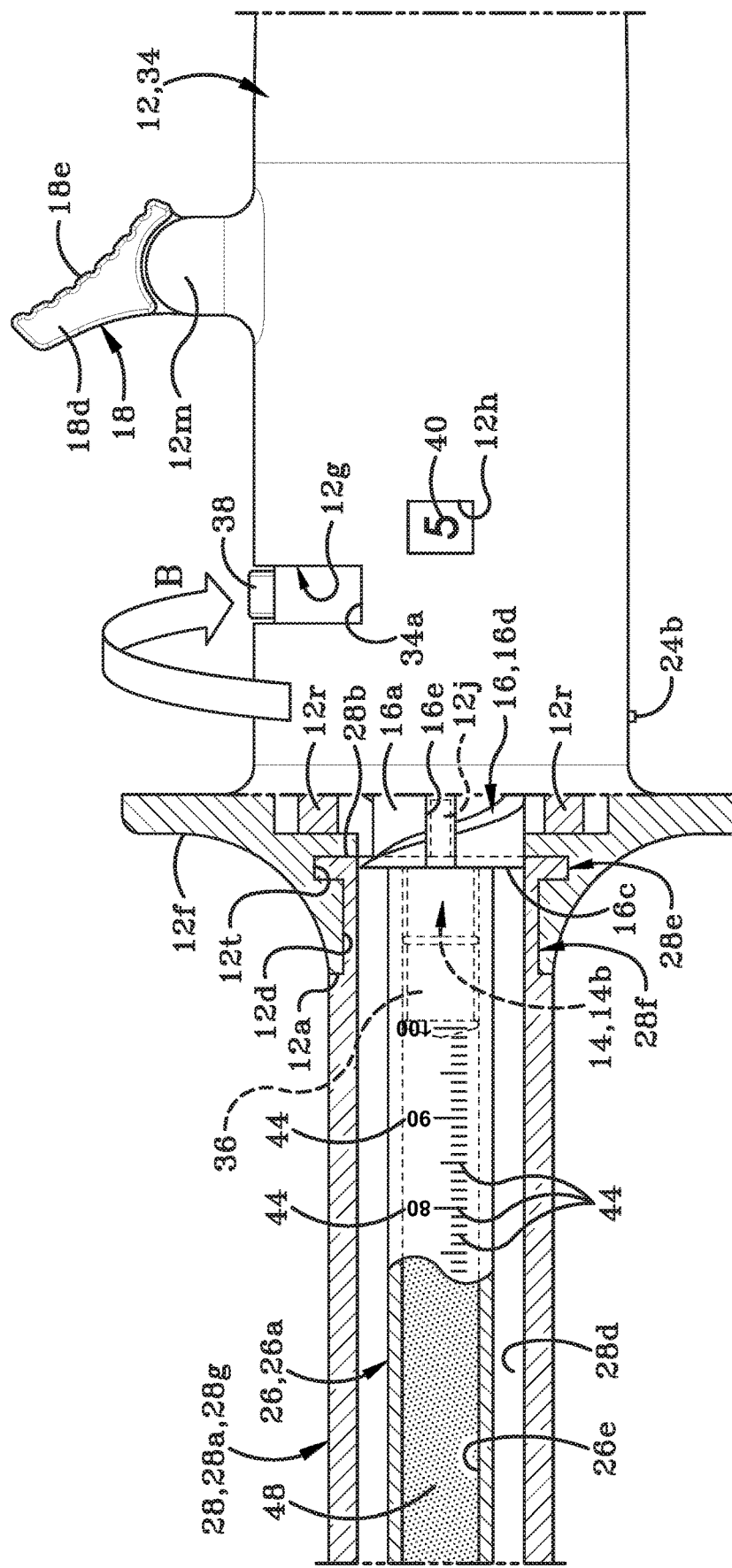
FIG. 15 is a partial longitudinal cross-section of the injecting device of FIG. 14 where the dose setting member has been rotated in a first direction so that a desired indicia is visible through an aperture defined in the housing.

The user determines the volume of medication they wish to dispense from injecting device 10 with each injection. For example, if the medication is BOTOX®, then the user likely will be administering a number of relatively small doses of BOTOX® to a patient. For example, a dose of around 0.1 cc may be administered to several different locations of a patient's forehead. In order to deliver a small dose of medication through needle 30, the user is able to pre-set the dosage to be delivered from injecting device 10 using dose setting member 22. The user holds housing 12 and pushes arm 38 in the direction indicated by direction marker 42, i.e., in the direction of arrow "B" (FIG. 15). As the arm 38 moves along slot 12g in the direction of arrow "B", dose setting member 22 is caused to rotate within interior cavity 12c of housing 12 about longitudinal axis "Y". Dose setting member 22 rotates in the same direction as the arm 38 is moved because arm 38 extends outwardly from dose setting member 22. Consequently, dose setting member 22 rotates in a first direction, i.e., the direction indicated by arrow "B".

It should be noted that dose setting member 22 rotates less than through one entire revolution around longitudinal axis "Y". The rotation of dose setting member 22 is limited by the length of slot 12g defined in housing. Slot 12g extends for less than one half of the circumference of the exterior surface of housing 12. Consequently, in one example, dose setting member 22 is able to rotate through less than about 180°. In one example, slot 12g extends for around one quarter of the circumference of the exterior surface of the housing 12. Consequently, in this example, dose setting member 22 is able to rotate through about 90° at most. During a dose setting operation where dose setting member 22 is rotated about the longitudinal axis "Y", the degree of rotation of dose setting member 22 is dictated by the selected dosage of liquid medication that the user wishes to deliver. In one example, the degree of rotation of dose setting member 22 may be about 5° up to about 180°. It will be understood that if slot 12g is longer than illustrated herein then dose setting member 22 may be rotated through more than 180°.

Rotation of dose setting member 22 in the first direction causes torsion spring 24 to become tightly wound around third region 22g thereof because first end 24a of torsion spring 24 is engaged with dose setting member 22. Dose setting member 22 is able to rotate in the first direction and relative to castle nut 20 because tip 22p of flange 22n is able to ride over gear teeth 20k of castle nut 20 because of the shape of the teeth 20k. Castle nut 20 remains in a fixed position because first leg 18f of actuator 18 is seated in one of the valleys 20i of castle nut 20. If the user releases arm 38, dose setting member 22 will be prevented from rotating back in a second and opposite direction to that indicated by arrow "B". The rotation in the second direction is prevented because tip 22p of flange 22n becomes locked between a pair of adjacent gear teeth 20k of castle nut 20.

Figure 14:
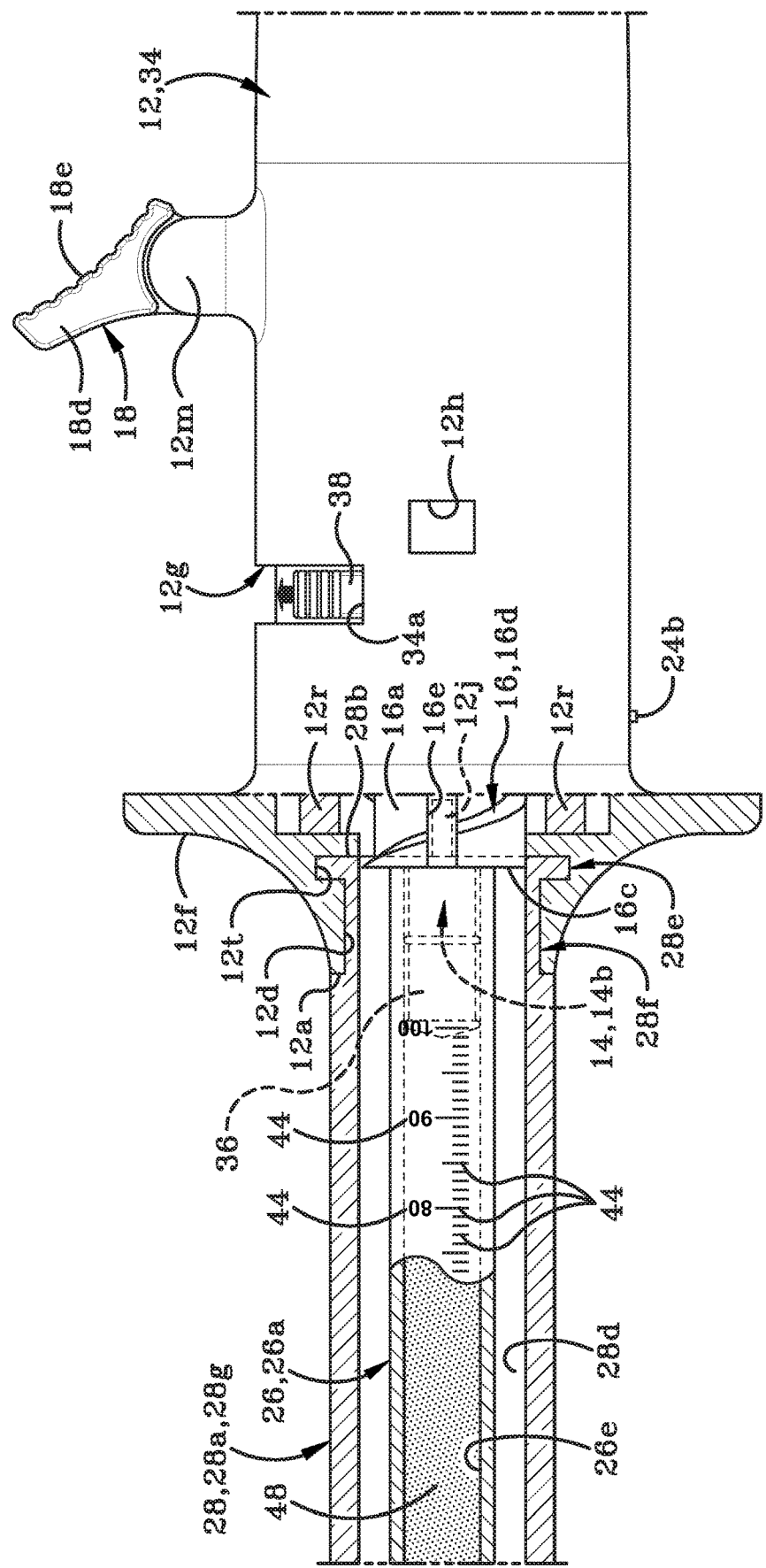
FIG. 14 is a partial longitudinal cross-section of the injecting device showing a quantity of fluid medication retained within the barrel and showing the dose setting member in an at-rest position.

In an initial at-rest position where dose setting member 22 has not been rotated (as is shown in FIG. 14), no indicia 40 are visible through aperture 12h. Additionally, second end 16c of feed tube 16 may be generally aligned with first end 28b of barrel housing 28. As dose setting member 22 rotates in the first direction (i.e., direction indicated by arrow "B") a first one of the indicia 40 on the exterior surface of dose setting member 22 will become visible through aperture 12h in housing 12. If the user continues to push on arm 38, a second one of the indicia 40 will become visible through aperture 12h, and then a third one of the indicia 40 and so on. The user will continue to push arm 38 in the direction of arrow "B" until the desired indicia 40 is visible through aperture 12h. For example, prior to pushing arm 38 in the direction "B", no indicia 40 are visible through aperture 12h. When the user pushes on arm 38 in the direction "B", the number "1" will become visible, then the number "2" will become visible, and so on. FIG. 15 shows the number "5" visible through aperture 12h. If this is the desired dosage that the user wishes to administer, the user will stop pushing on arm 38. As described above, the dose setting member 22 does not rotate in the opposite second direction when arm 38 is no longer being pushed because tip 22p engages gear teeth 20k on the stationary castle nut 20 and thereby locks dose setting member 22 against rotation in second direction. In summary, the user is able to select the desired dosage by pushing on arm 38 and when arm 38 is released, the selection is set. If the user determines they have not selected a high enough dosage, they are able to push arm 38 further along slot 12g to the correct dosage and then release arm 38.

At this stage, injecting device 10 is armed for dispensing the pre-set dose of medication through needle 30. It should be noted that pushing on head 14a of plunger 14 at this point will not result in plunger 14 being able to move forward toward housing 12. This forward movement is prevented because feed tube 16 is engaged with threads 20j of castle nut 20 and, as explained above, castle nut 20 is locked against movement by first leg 18f of actuator 18.

Figure 16:
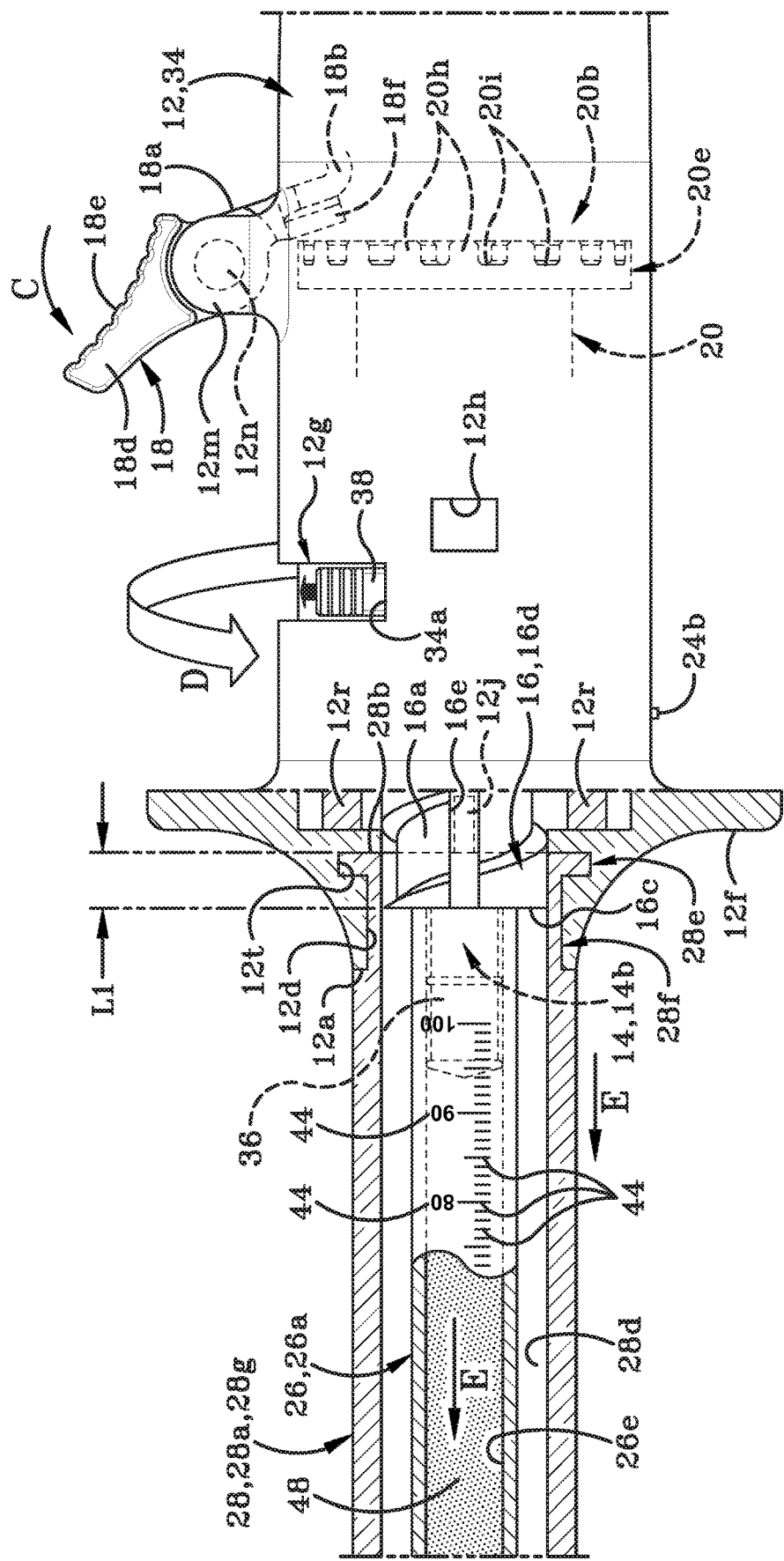
FIG. 16 is a partial longitudinal cross-section of the injecting device where the actuator is pivoting out of engagement with the castle nut, the dose setting member is rotating in the second direction, and the plunger is pushing a volume of fluid medication out of the barrel.
Figure 17:
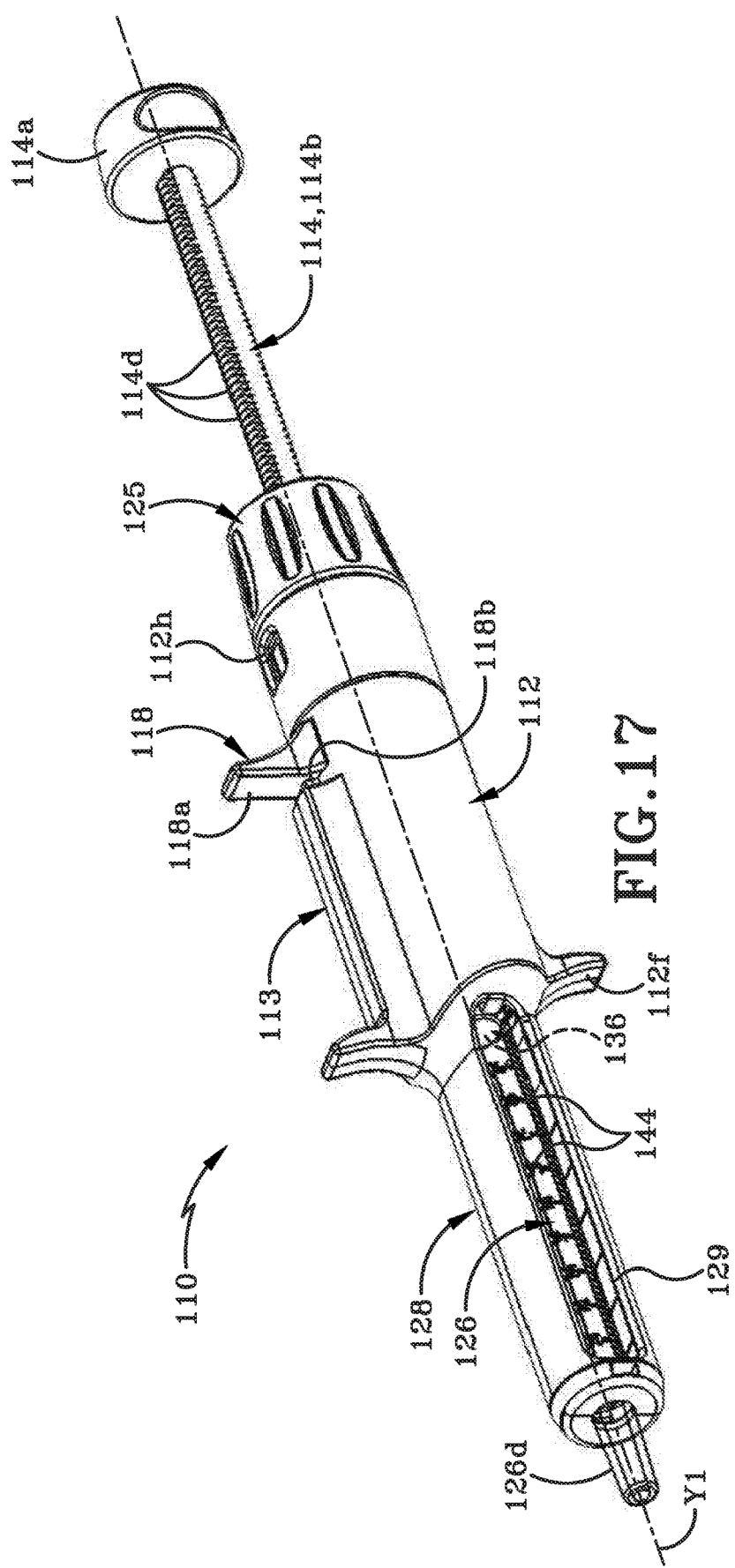
FIG. 17 is an isometric perspective view of a second embodiment of an injecting device in accordance with an aspect of the present disclosure.

When the user is ready to administer the medication from injecting device 10, he or she will insert the tip 30a of needle 30 to the correct depth in the patient's skin or body. The user will then push actuator 18 in the direction indicated by arrow "C" (FIG. 16). This will result in head 18a of actuator 18 pivoting about pivot rod 20n and moving first leg 18f out of the valley 20i within which first leg 18f was previously seated. Moving first leg 18f out of the valley 20i leaves castle nut 20 free to rotate in either of the first direction or the second direction. As indicated earlier herein, torsion spring 24 was previously tightly wound around third region 22g of dose setting member 22 when dose setting member 22 was rotated in the direction of arrow "B". As soon as castle nut 20 is released to rotate, the dose setting member 22 is also released to rotate since dose setting member is locked against rotation by castle nut 20. The spring force in torsion spring 24 causes the spring to return to its less-wound, at-rest position. Because dose setting member 22 is interlocking engaged with torsion spring 24, as torsion spring 24 returns to its at-rest position, dose setting member 22 is caused to rotate in the second direction, i.e., in a direction opposite to arrow "B". This rotation in the second direction is indicated by arrow "D" in FIG. 16.

Rotation of dose setting member 22 in the direction of arrow "D" causes simultaneously rotation of castle nut 20 in the direction of arrow "D" because of the interlocking of tip 22p with gear teeth 20k. Rotation of castle nut 20 in the direction of arrow "D" results in the threads 20*j* of castle nut 20 rotating and this in turn causes feed tube 16 (which is threadedly engaged with threads 20*j*) to be drawn forwardly within housing 12 in the direction indicated by arrow "E" in FIG. 16. As is shown in FIG. 16, second end 16*c* of feed tube 16 has moved forwardly within bore 28*d* of barrel housing 28 and may now be located a distance "L1" forwardly of first end 28*b* of barrel housing 28.

As indicated earlier herein, feed tube 16 is interlockingly engaged with plunger 14 via the engagement of teeth 16*h* with ridges 14*d*. As feed tube 16 moves forwardly through bore 20*d* of castle nut 20, through bore 22*d* of dose setting member 22, and into bore 28*d* of housing 28 in the direction of arrow "E", by a distance "L1" then plunger 14 is moved in unison therewith and also moves forwardly in the direction of arrow "E" through a distance of "L1". The region of feed tube 16 that includes second end 16*c* moves between the interior surface of barrel housing 28 and the exterior surface of barrel 26 while free end 14*c* of plunger 14 that includes tip 36 moves within the bore 26*e* of barrel 26. As plunger 14 moves forwardly in the direction of arrow "E", the tip 36 moves forwardly within bore 26*e* in the direction of arrow "E" and pushes the pre-set dose of medication out of needle 30 and into the patient's skin or body.

When the torsion spring 24 has returned to its at-rest position, rotation of dose setting member 22 and castle nut 20 will cease and forward movement of plunger 14 will cease. The user breaks contact with actuator 18 and first leg 18*f* of actuator 18 will again become seated in one of the valleys 20*i* of castle nut 20, locking castle nut 20 and thereby dose setting member 22 against rotation in the second direction (i.e., direction "D"). It should also be noted that as dose setting member 22 rotates in the second direction "D", arm 38 moves along slot 12*g* and back to its at-rest position, i.e., where no indicia 40 are visible through aperture 12*h*.

Once the first dose of medication has been administered as described above, the user will withdraw needle 30 from the patient's body and will re-arm the injecting device to deliver any pre-set dose of medication by pushing arm 38 in the direction of arrow "A" once again. The user will then repeat the steps described above in order to administer a second pre-set dose of medication and will again repeat these steps to administer any subsequent pre-set doses of medication.

It will be understood that pushing arm 38 further along slot 12*g* in housing 12 will cause a greater degree of rotation of dose setting member 22 and therefore will wind torsion spring 24 up to a greater extent than will pushing arm 38 a shorter distance along slot 12*g*. Pushing the arm 38 so that the first of the indicia 40 is displayed in aperture 12*h* will result in the torsion spring 24 being wound to the least possible extent and therefore the plunger 14 will be caused to move a relatively small distance within bore 26*e* of barrel 26 and thereby deliver a smaller dose of medication. If arm 38 is pushed along slot 12*g* to a sufficient degree that the last of the indicia 40 (i.e., the number "6" in the illustrated figures) is displayed in aperture 12*h*, then dose setting member 22 is rotated to the greatest possible extent in the first direction and therefore the torsion spring 24 is wound to the greatest possible extent. In this instance the plunger 14 is moved the greatest distance within bore 26*e* of barrel 26 when actuator 18 is depressed and, therefore, the largest possible pre-set dose of medication is administered to the patient.

The injecting device 10 therefore makes it possible for the user to consistently administer the correct pre-set dose of medication to a patient. Provided the dose setting member 22 is rotated to the correct desired indicia setting, the correct desired dose of medication will be delivered.

It should be noted that during use of injecting device 10, neither the dose setting member 22 nor the castle nut 20 move axially within housing 12. In other words, neither dose setting member 22 nor castle nut 20 move in a direction parallel to the longitudinal axis "Y" between first end 12*a* and second end 12*b* of housing 12. The only movement of dose setting member 22 and castle nut 20 is one of rotation about the longitudinal axis "Y".

It should further be noted that during use of injecting device 10, feed tube 16 and plunger 14 move axially within housing 12. In other words, feed tube 16 and plunger 14 move along or parallel to the longitudinal axis "Y" and between first end 12*a* and second end 12*b* of housing 12. When an initial dose of medication is drawn from a bottle of medication, plunger 14 is pulled axially rearwardly away from housing 12 and in a direction parallel to the longitudinal axis "Y". When dose setting member 22 has been rotated to pre-set a dosage to be delivered and actuator 18 has been activated to pivot first leg 18*f* out of the associated valley 20*i* of castle nut 20, castle nut 20 rotates about the longitudinal axis "Y" in the second direction and feed tube 16 moves axially and forwardly within housing 12 and parallel to longitudinal axis "Y".

It is further noted that the interior surfaces of first and second housing sections 32, 34 are free of any threads that might engage plunger 14, feed tube 16, castle nut 18, dose setting member 22, torsion spring 24, barrel 26, or barrel housing 28. Furthermore, none of plunger 14, feed tube 16, castle nut 18, dose setting member 22, torsion spring 24, barrel 26, or barrel housing 28 have external threads that engage any threaded interior surface of first and second housing sections 32, 34. The only components that are threaded are feed tube 16 that has external threads 16*d* and castle nut 20 that has internal threads 20*j*.

It will be understood that in other examples, dose setting member 22 may be provided with internal threads to engage threads 16*d* on feed tube 16 instead of or in addition to internal threads 20*j* of castle nut 20.

While it has been disclosed herein that arm 38 may be pushed along slot 12*g* to cause rotation of dose setting member 22, it will be understood that arm 38 may be held stationary between the user's fingertips and housing 12 may instead be rotated so that slot 12*g* moves relative to the stationary arm 38.

Referring to FIGS. 17-24, there is shown a second embodiment of an injecting device in accordance with the present disclosure, generally indicated at 110. Injecting device 110 is substantially similar to injecting device 10 and is useful for the same purpose, i.e., for providing a capability to pre-set a desired dosage of fluid to be delivered from injecting device 10.

Injecting device 110 includes a number of components that are substantially identical or substantially similar to components within injecting device 10. Housing 112 of injecting device 110 may be of a generally similar configuration to housing 12 but also includes features not present in housing 12. Firstly, housing 112 may be fabricated as a single unitary component or may be comprised of first and second housing sections that are secured together. Housing 112 may include a region that is molded to ultimately form collar 112*f* in a similar fashion to the regions of housing sections 32, 34 that form collar 12*f*. Housing 112 includes a region that extends upwardly and outwardly from a circumferential surface of housing 112 to form a substantially U-shaped extension 113. Extension 113 defines a longitudinally-extending channel (not shown) therein that is configured to receive an elongate, longitudinally-extending arm 118*b* of actuator 118 therein. Actuator 118 will be further discussed later herein. Housing 112 does not include an opening similar to slot 12*g* but does include an aperture 112*h* similar to aperture 12*h*.

Injecting device 110 also includes a plunger 114 that is substantially identical in structure and function to plunger 14. Plunger 114 has a head 114*a* and a shaft 114*b* that terminates in a free end 114*c* (FIG. 22) and with which a sealing tip 136 (FIG. 17) is engaged. (Head 114*a* has a slightly different configuration to head 14 as is evident from comparing FIG. 1 with FIG. 17.)

Injecting device 110 also includes a feed tube 116 that is substantially identical in structure and function to feed tube 16. Plunger shaft 114*b* is inserted through the bore 116*f* of feed tube 116. The plunger shaft 114*b* includes a plurality of ridges 114*d* formed thereon and teeth 116*h* (FIG. 19) on flaps 116*i* of feed tube 116 engages ridges 114*d* on plunger 114 in a similar way to the way teeth 16*h* on flaps 16*i* engage ridges 14*d* on plunger 14.

Actuator 118 includes a head 118*a* that is substantially identical to head 18*a* on actuator 18. An arm 118*b* extends outwardly from head 118*a* in such a way that when actuator 118 is engaged with housing 112, arm 118*b* will be oriented generally parallel to the longitudinal axis "Y1" (FIGS. 17 and 23) of injecting device 110. Arm 118*b* is configured to be received within the channel defined by extension 113 on housing 112. A finger 118*c* extends outwardly from an end of arm 118*b* remote from head 118*a*. Finger 118*c* may be configured to be one or more alternating ridges and valleys so that finger 118*c* appears as a wave when viewed from above as in FIG. 22. An end 118*d* is provided on finger 118*c* and a leg 118*e* (FIG. 23) extends downwardly from finger 118*c* a distance longitudinally inwardly from end 118*d*. End 118*d* may be affixed to the interior surface of extension 113. Leg 118*e* is of a substantially complementary shape and size to one of the valleys 120*i* (FIGS. 19 and 20) of a castle nut 120. Leg 118*e* is configured to be selectively seated in one of the valleys 120*i* of castle nut 120, as will be later described herein.

Figure 20:
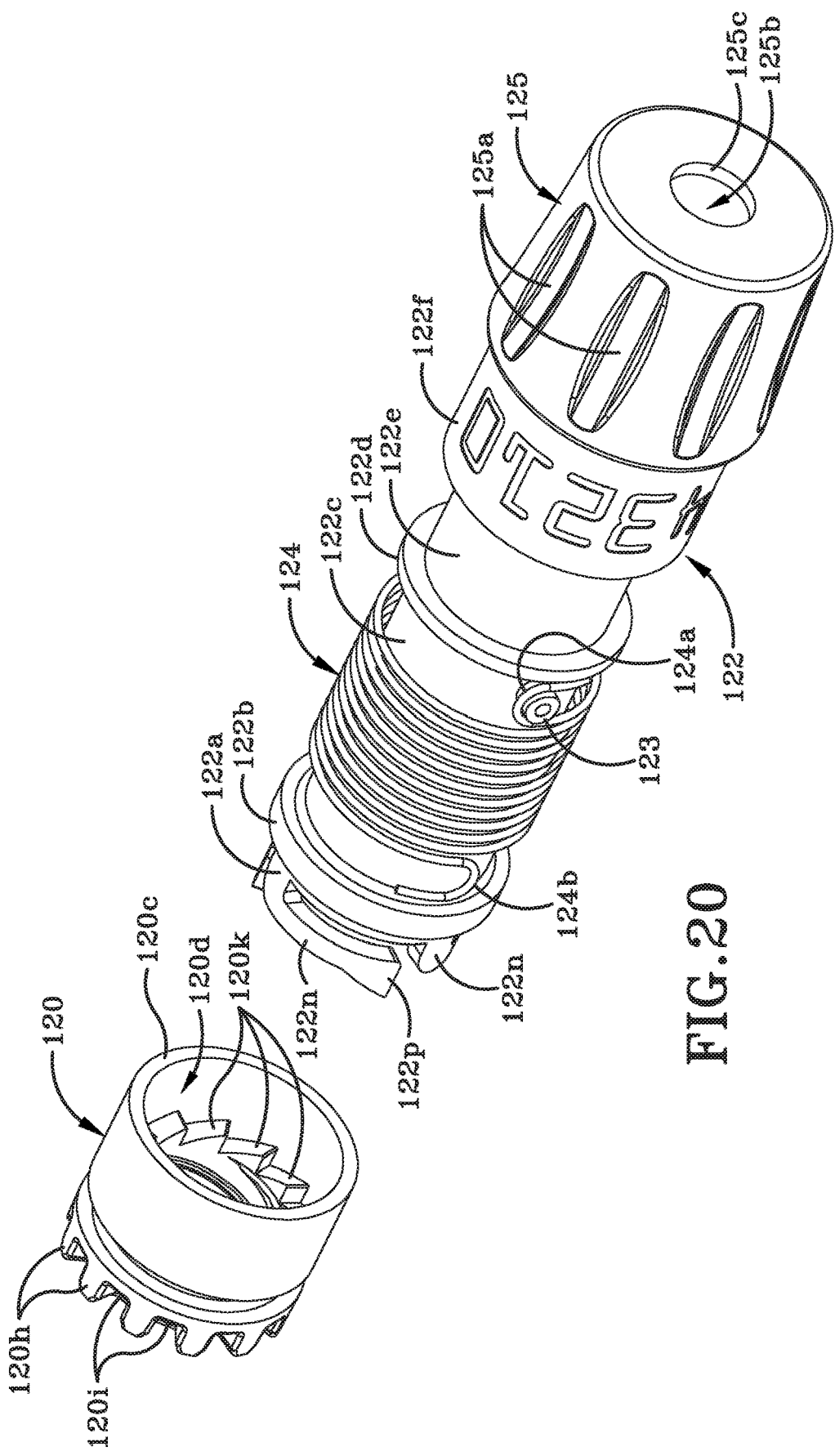
FIG. 20 is a partially exploded rear isometric perspective view of the injecting device of FIG. 18.
Figure 21:
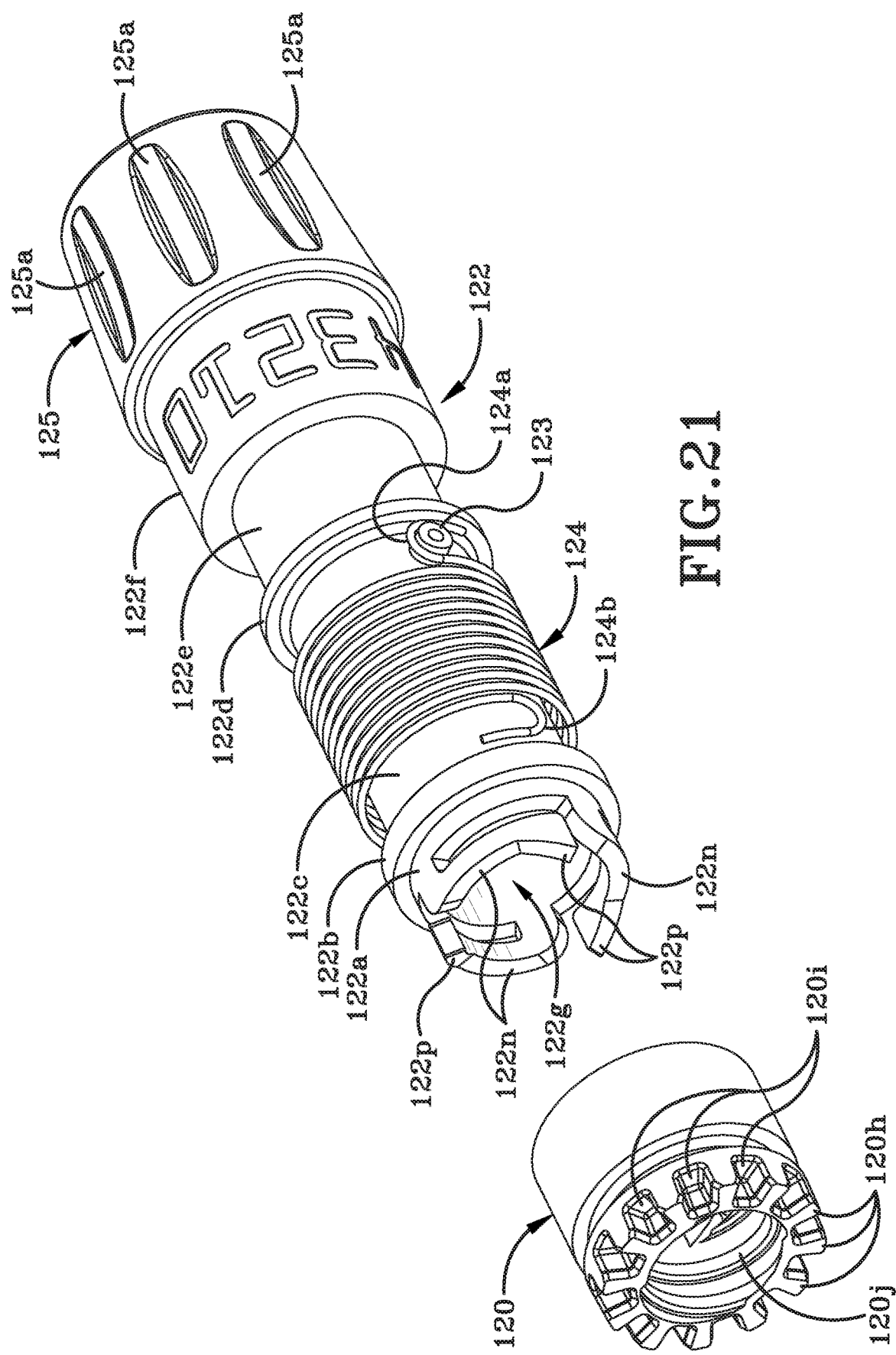
FIG. 21 is a front isometric perspective view of the injecting device shown in FIG. 20.
Figure 22:
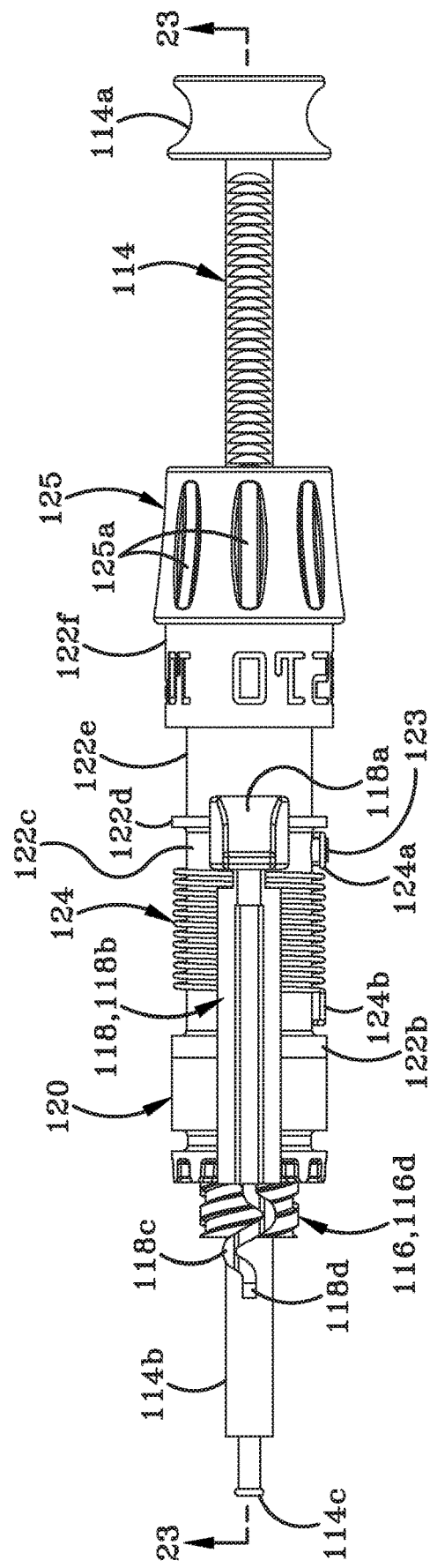
FIG. 22 is a side elevational view of the injecting device as shown in FIG. 18.

Castle nut 120 is substantially identical in structure and function to castle nut 20 of injecting device 10 and therefore will not be described in any additional detail except to state that an interior wall of castle nut 120 which defines bore 120*d* is internally threaded with threads 120*j*. Feed tube 116 is inserted through bore 120*d* and threads 120*j* on castle nut 120 threadedly engage threads 116*d* on feed tube 116 in the same way that threads 20*j* on castle nut 20 engage threads 16*d* on feed tube 16. Furthermore, as shown in FIGS. 20 and 21, castle nut 120 includes a plurality of alternating ridges 120*h* and valleys 120*i* that are substantially identical in structure and function to ridges 20*h* and valleys 20*i* on castle nut 20. As indicated above, the interlocking engagement of actuator 118 and castle nut 120 will be described later herein.

Figure 19:
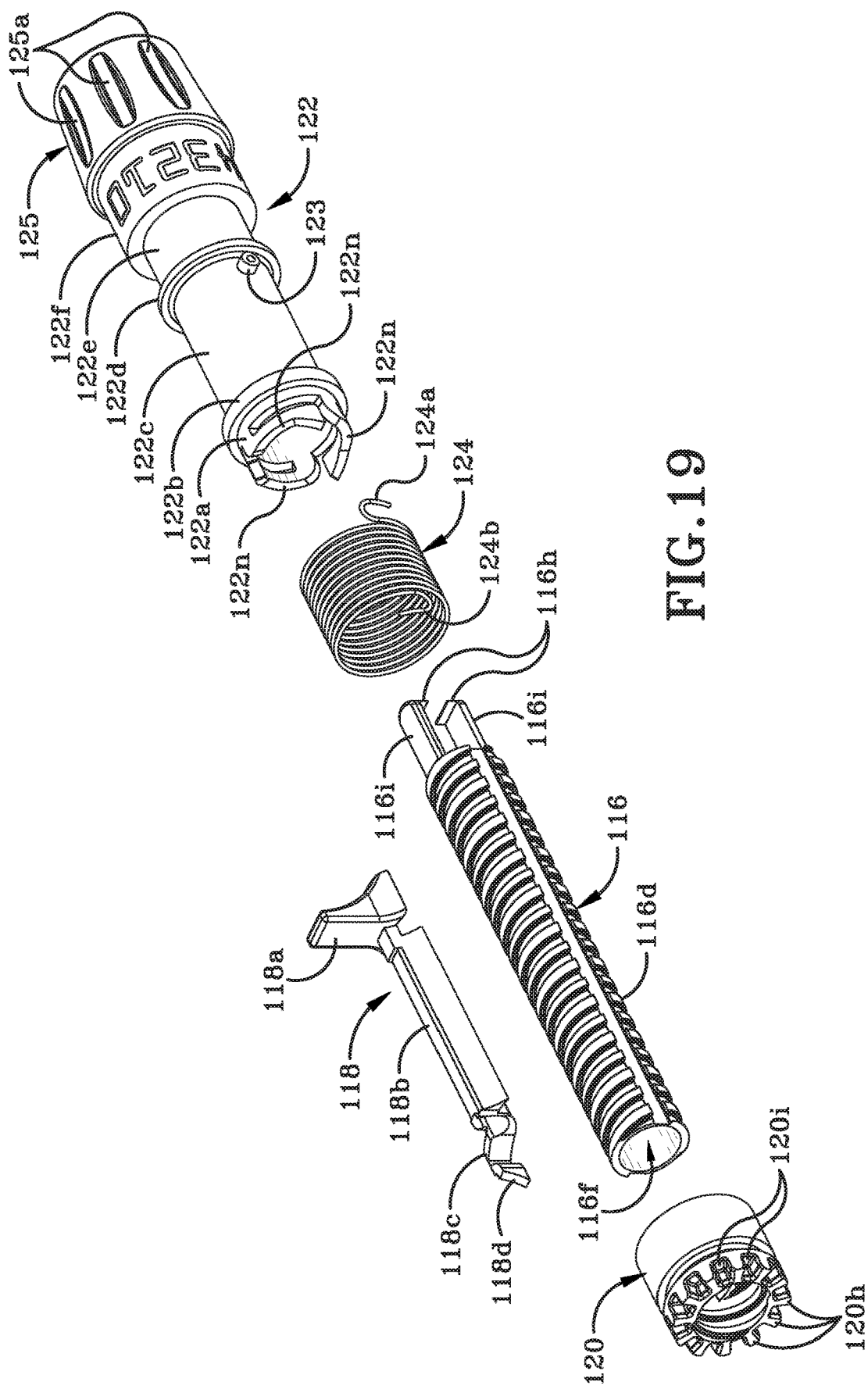
FIG. 19 is an exploded isometric perspective view of the injecting device shown in FIG. 18.

Injecting device 110 further includes a dose setting member 122 that is different in some regards to dose setting member 22 of injecting device 10 but also has some similarities to dose setting member 22. As best seen in FIG. 19, dose setting member 122 includes a first region 122*a*, a second region 122*b*, a third region 122*c*, a fourth region 122*d*, a fifth region 122*e*, and a sixth region 122*f* that may be fabricated as a single, unitary, monolithic component. First region 122*a*, third region 122*c*, and fifth region 122*e* are each of a substantially similar external diameter. Similarly, second region 122*b*, fourth region 122*d*, and sixth region 122*f* are also each of a substantially similar external diameter.

As best seen in FIG. 19, first region 122*a* includes one or more actuate flanges 122*n* that have tips 122*p* that are configured to interlock with the gear teeth 120*k* in bore 120*d* of castle nut 120 when dose setting member 122 engages castle nut 120.

Second region 122*b* is configured to abut a second end 120*c* of castle nut 120 when first region 122*a* of dose setting member 122 is inserted into a complementary region of bore 120*d* of castle nut 120.

Figure 18:
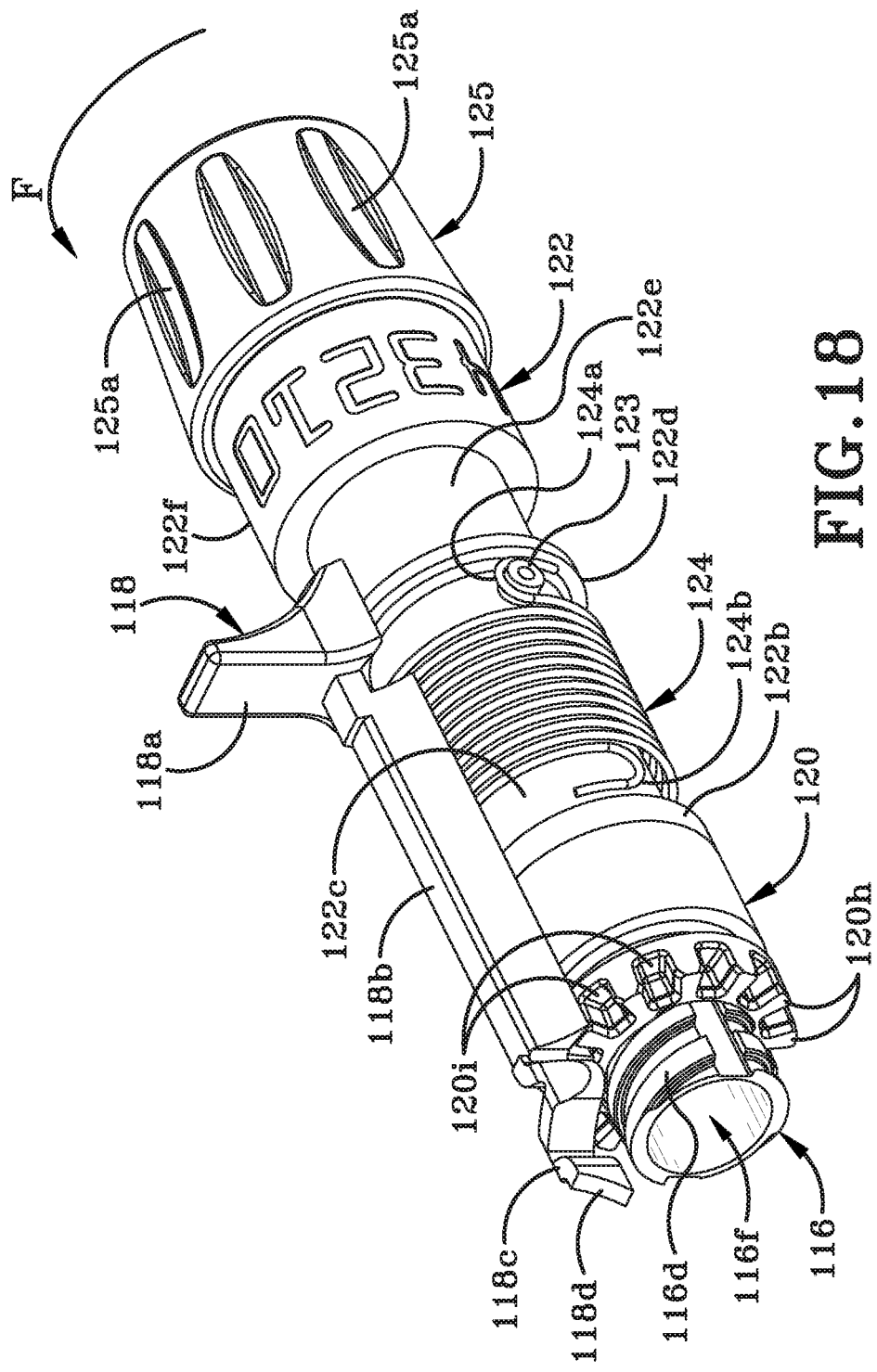
FIG. 18 is a partial isometric perspective view of the injecting device of FIG. 17 except that the housing, the barrel, the barrel housing, and the plunger shown in FIG. 17 are not illustrated.

Third region 122*c* includes a post 123 that extends radially outwardly therefrom. A torsion spring 124 is positioned around an exterior surface of third region 122*c*. A first end 124*a* (FIG. 19) of torsion spring 124 wraps around post 123 as is illustrated in FIG. 18. A second end 124*b* of torsion spring 124 may be engaged with a region of housing 112 or with any other non-rotatable component within housing 112.

Fourth region 122*d* may be seated within a complementary channel defined in the interior surface of housing 112 in a similar way to how fourth region 22*h* of dose setting member 22 engages in channel 12*k'* defined between walls 12*k* of housing 12. The engagement of fourth region 122*d* with a complementary channel in housing 112 prevents dose setting member 122 from moving along longitudinal axis, i.e., axially, during use of injecting device 110.

Sixth region 122*f* includes a plurality of indicia 140 provided on an exterior surface thereof. The indicia 140 similar to indicia 40, are oriented in a single row where the row is oriented at right angles to longitudinal axis "Y1". The indicia are radially aligned with each other. The row of indicia is aligned with aperture 112*h* defined in housing 112. Only one indicia 40 at a time will be visible through aperture 112*h* when dose setting member 122 is rotated within housing 112, as will be described hereafter. Each indicia 140, like indicia 40, represents one unit of measurement of a dosage of a fluid to be administered using injecting device 10.

Instead of an arm, like arm 38, extending radially outwardly from dose setting member 122, dose setting member 122 is interlockingly engaged with a dial member 125. Dial member 125 may be fixedly engaged with dose setting member 122 in any suitable manner or may be formed as an integral part of dose setting member 122. If dial member 125 is a separate component, dial member 125 may include a region that friction-fits inside an enlarged region of bore 122*g* (FIG. 23) defined by sixth region 122*f* of dose setting member 122. (Bore 122*g* extends from one end of dose setting member 122 to the other.) In other examples, dial member 125 may be adhesively engaged with sixth region 122*f*. Dial member 125 may include an exterior surface that has some type of texturing thereon that increases the ability of a user to grip dial member 125. For example, dial member 125 may include a plurality of grooves 125*a* (FIG. 19) thereon, or a plurality of ridges, or knurling, or any other type of textured finish.

As best seen in FIG. 23, dial member 125 defines a bore 125*b* therein that extends from one end of dial member 125 to the other end. The end of dial member 125 proximate plunger head 114*a* defines an opening 125*c* to bore 125*b*.

Injecting device 110 also includes a barrel 126 that is substantially identical in structure and function to barrel 26. Barrel 126 defines a bore (not numbered) therein and within which the tip 136 and a section of plunger shaft 114*b* are received. A plurality of graduations 144 are provided on the exterior surface of barrel 126 and these graduations 144, like graduations 44, indicate a volume of fluid retained within the bore of the barrel 126.

Barrel housing 128 is substantially identical to barrel housing 28 in structure and function except that barrel housing 128 defines a window 129 therein and through which a portion of the barrel 126 is visible. In particular, the portion of barrel 126 that includes graduations 144 may be visible through window 129. Barrel 126 interlockingly engages with barrel housing 128 in a substantially identical manner to the way barrel 26 engages with barrel housing 28. When barrel 126 is engaged with barrel housing 128, the needle hub 126d extends outwardly from an opening defined in an end of barrel housing 128. Although not illustrated in FIG. 17, it will be understood that a hollow needle may be engaged in needle hub 126d. The hollow needle will be placed in fluid communication with the bore of barrel 126 when the needle is engaged with needle hub 126d.

Injecting device 110 is used in a substantially identical manner to injecting device 10 except for how dose setting member 122 is caused to rotate in a first direction to pre-set a dose of fluid to be delivered by injecting device 110, and how actuator 118 functions.

As has been described previously herein, dose setting member 22 is caused to rotate in a first direction by a user pushing arm 38 along slot 12g in housing 12. Dose setting member 122 is caused to rotate within the interior cavity of housing 112 by rotating dial member 125 in a first direction as indicated by arrow "F" in FIG. 18. Because dial member 125 is fixedly engaged with dose setting member 122, when dial member 125 is rotated in the first direction "F", the dose setting member 122 will also be rotated in the first direction "F". As dose setting member 122 rotates, torsion spring 124 will become more tightly wound and will store up energy therein. Additionally, as dose setting member 122 rotates the indicia 140 will sequentially be displayed in aperture 112h. Initially, the number "0" may be displayed but as dial member 125 is rotated in the first direction "F", the indicia will sequentially increase, i.e., first the number "1" will become visible through aperture 112h, then the number "2", then "3" and so on.

The user will rotate dial member 125 in the first direction "F" until the desired indicia 140 is visible through aperture 112h. Similar to dose setting member 22, when dose setting member 122 is rotated in the first direction "F", the flanges 122n, particularly the tips 122p thereof ride readily over gear teeth 120k of castle gear 120. When dial member 125 is released, the rotation of dial member 125 and therefor the rotation of dose setting member 122 in the first direction "F" will cease, and tips 122p of flanges 122n will become interlocked with gear teeth 120k on castle nut 120. This interlocking engagement will prevent dose setting member 122 from rotating in an opposite or second direction for reasons explained hereafter.

As is illustrated in FIGS. 23 and 24, actuator 118 is slidable in one of a first longitudinal direction "G" and a second longitudinal direction "H". When actuator 118 is moved in the first longitudinal direction "G", leg 118e becomes seated within one of the valleys 120i on castle nut 120. This seating of leg 118e in valley 120i prevents castle nut 120 from rotating in either of the first direction "F" or in a second direction opposite to direction "F". When actuator 118 is moved in the second longitudinal direction "H", leg 118e moves out of its engagement with castle nut 120. This disengagement permits castle nut 120 to rotate. Movement of actuator 118 in the second longitudinal direction "H" also causes the finger 118c on actuator to be compressed against an interior front end surface of extension 113 of housing 112. When the user releases actuator 118, the spring force stored in finger 118c causes actuator 118 to move once again in the first longitudinal direction "G", once again seating leg 118e in one of the valleys 120i of castle nut, thereby preventing rotation of castle nut 120 once again.

When dose setting member 122 has been rotated in the first direction "F" as described above, first leg 118e of actuator 118 is seated within a valley 120i of castle nut 120 and therefore dose setting member 122 rotates relative to castle nut 120 which remains in a fixed position. When the user releases the dial member 125, the castle nut 120 is still fixed in position against rotation because the leg 118e is seated in one of the valleys 120i. Consequently, when the tip 122p of dose setting member 122 interlocks with the gear teeth 120k, the fixed condition of castle nut 120 prevents both the castle nut 120 and the dose setting member 122 from rotating in the second direction. Consequently, the size of the dose of fluid that is able to be delivered by injecting device is set.

When the user is ready to administer the pre-set dose, he or she will contact actuator 118 and will push actuator head 118a in the direction indicated by arrow "H" toward collar 112h of housing 112. This force on actuator 118 causes leg 118e of actuator 118 to disengage from castle nut 120 as described above. Castle nut 120 is then released to rotate. Torsion spring 124 begins to return to its at rest position and, as it does so, torsion spring 124 causes dose setting member 122 (and thereby castle nut 120 and dial member 125) to rotate in a second direction, i.e., the opposite direction to that indicated by arrow "F" in FIG. 18.

Rotation of castle nut 120 causes feed tube 116 (which is threadably engaged with castle nut 120) to be moved in the same second longitudinal direction "H" as actuator 118 has been pushed. As feed tube 116 moves longitudinally through bore 120d of castle nut 120, the plunger 114 is moved longitudinally forwardly in unison therewith in the direction of arrow "H". The tip 136 of plunger 114 moves forwardly within the bore of barrel 126 in the direction of arrow "H" and, consequently, a volume of liquid within the bore of barrel 126 is pushed outwardly through a hollow needle engaged with needle hub 126d. The plunger 114 will continue to move in the direction of arrow "H" until the torsion spring 124 and thereby the dose setting member 122 have returned to their at-rest positions.

Various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal", "lateral" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed herein could be termed a second feature/element, and similarly, a second feature/element discussed herein could be termed a first feature/element without departing from the teachings of the present invention.

An embodiment is an implementation or example of the present disclosure. Reference in the specification to "an embodiment," "one embodiment," "some embodiments," "one particular embodiment," or "other embodiments," or the like, means that a particular feature, structure, or characteristic described in connection with the embodiments is included in at least some embodiments, but not necessarily all embodiments, of the invention. The various appearances "an embodiment," "one embodiment," "some embodiments," "one particular embodiment," or "other embodiments," or the like, are not necessarily all referring to the same embodiments.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/–0. % of the stated value (or range of values), +/–1% of the stated value (or range of values), +/–2% of the stated value (or range of values), +/–5% of the stated value (or range of values), +/–10% of the stated value (or range of values), etc. Any numerical range recited herein is intended to include all sub-ranges subsumed therein.

Additionally, any method of performing the present disclosure may occur in a sequence different than those described herein. Accordingly, no sequence of the method should be read as a limitation unless explicitly stated. It is recognizable that performing some of the steps of the method in a different order could achieve a similar result.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

What is claimed:

1. An injecting device comprising:
    a housing having a first end and a second end, and a longitudinal axis extending therebetween; wherein an interior surface of said housing bounds and defines an interior cavity;
    a dose setting member positioned within the interior cavity and being rotatable in one of a first direction and a second direction about the longitudinal axis;
    a plunger extending through a bore of the dose setting member; said plunger extending one of along the longitudinal axis and parallel to the longitudinal axis;
    a barrel extending outwardly from the first end of the housing and defining a barrel bore that is adapted to hold a volume of liquid therein; wherein a tip of the plunger is received with the barrel bore; wherein rotation of the dose setting member in the second direction causes the plunger to move axially within the barrel bore; and
    wherein the dose setting member remains in a substantially constant axial position within the interior cavity of the housing during rotation of the dose setting member in each of the first direction and the second direction.

2. The injecting device according to claim 1, wherein the housing defines an aperture therein that extends between the interior surface and an exterior surface of the housing, and wherein an exterior surface of the dose setting member includes a plurality of indicia thereon, and wherein rotation of the dose setting member in each of the first direction and the second direction causes the plurality of indicia to be sequentially visible through the aperture.

3. The injecting device according to claim 2, wherein the aperture is located a distance rearwardly from the first end of the housing; and wherein each indicia of the plurality of indicia is displayed at substantially the same distance from the first end of the housing.

4. The injecting device according to claim 2, wherein the indicia of the plurality of indicia are arranged in a single row on the exterior surface of the dose setting member; and wherein the single row is oriented at right angles to the longitudinal axis.

5. The injecting device according to claim 2, wherein the indicia of the plurality of indicia are radially aligned with each other.

6. The injecting device according to claim 1, further comprising a slot defined between the interior surface and an exterior surface of the housing, wherein the slot is oriented at right angles to the longitudinal axis; and wherein an arm extends outwardly from the dose setting member and extends through the slot.

7. The injecting device according to claim 6, further comprising:
    an aperture defined between the interior surface and the exterior surface of the housing; wherein the aperture is located proximate the slot;
    a plurality of indicia provided on the dose setting member proximate the arm; wherein the plurality of indicia are oriented at right angles to the longitudinal axis; and during rotation of the dose setting member the arm travels along the slot and the indicia are sequentially visible through the aperture.

8. The injecting device according to claim 1, further comprising an actuator operatively engaged with the dose setting member; wherein the actuator is selectively movable between an engaged position and a disengaged position; and when in the engaged position, the actuator prevents rotation of the dose setting member in the second direction; and when the actuator is in the disengaged position, the dose setting member is rotatable in the second direction.

9. The injecting device according to claim 1, further comprising a castle nut provided within the interior cavity of the housing; wherein the castle nut is operatively engaged with the dose setting member; and wherein the castle nut is selectively rotatable in unison with the dose setting member in the second direction about the longitudinal axis.

10. The injecting device according to claim 9, wherein the castle nut and dose setting member are engaged with each other through a geared connection.

11. The injecting device according to claim 10, wherein the castle nut remains in a substantially constant axial position during rotation of the dose setting member in each of the first direction and the second direction about the longitudinal axis.

12. The injecting device according to claim 9, further comprising an actuator operatively engaged with the castle nut; wherein the actuator is selectively movable between an engaged position and a disengaged position relative to the castle nut; and when in the engaged position, the actuator prevents castle nut from rotating in each of the first direction and the second direction; and when the actuator is in the disengaged position, the castle nut is rotatable in one of the first direction and the second direction.

13. The injecting device according to claim 12, wherein the actuator is pivotable between the engaged position and the disengaged position.

14. The injecting device according to claim 9, further comprising a feed tube having an exterior surface provided with threads; and wherein an interior surface of the castle nut bounds and defines a bore, and the interior surface of the castle nut is provided with threads; and wherein the feed tube is received within the bore of the castle nut and the threads of the feed tube engage the threads of the castle nut.

15. The injecting device according to claim 14, wherein the feed tube moves one of along the longitudinal axis and parallel to the longitudinal axis when the castle nut is rotated about the longitudinal axis.

16. The injecting device according to claim 15, wherein the feed tube defines a bore therein, and the plunger is received through the bore of the feed tube.

17. The injecting device according to claim 16, further comprising a plurality of ridges provided on an exterior surface of the plunger and one or more teeth provided on the feed tube; wherein the plurality of ridges and the one or more teeth operatively engage the plunger and the feed tube together.

18. The injecting device according to claim 14, further comprising a barrel housing defining a barrel housing bore therein; wherein the barrel is seated within the barrel housing bore; and wherein the feed tube defines a feed tube bore therein; and when the dose setting member rotates in the second direction, a portion of the feed tube moves axially into the barrel housing bore and a portion of the barrel is received in the feed tube bore.

19. The injecting device according to claim 1, wherein the dose setting member is rotatable through less than one full revolution about the longitudinal axis.

\* \* \* \* \*